United States Patent
Gagnon et al.

(10) Patent No.: US 7,423,114 B2
(45) Date of Patent: Sep. 9, 2008

(54) GD2 LIGANDS

(75) Inventors: Martin Gagnon, Montreal (CA); H. Uri Saragovi, Montreal (CA)

(73) Assignee: McGill University, Montreal, Quebec (CA)

( * ) Notice: Subject to any disclaimer, the term of this patent is extended or adjusted under 35 U.S.C. 154(b) by 0 days.

(21) Appl. No.: 10/528,542

(22) Filed: Nov. 28, 2005

(65) Prior Publication Data

US 2006/0159652 A1    Jul. 20, 2006

Related U.S. Application Data

(60) Provisional application No. 60/412,492, filed on Sep. 20, 2002.

(51) Int. Cl.
*A61K 38/04* (2006.01)
*A61K 38/00* (2006.01)
*C07K 5/00* (2006.01)
*C07K 7/00* (2006.01)
*C07K 16/00* (2006.01)
*C07K 17/00* (2006.01)

(52) U.S. Cl. .................. 530/327; 514/14; 424/85.1; 424/1.69

(58) Field of Classification Search .......... 514/2
See application file for complete search history.

(56) References Cited

OTHER PUBLICATIONS

Helfand S. C., Hank J. A., Gan J., and Sondel P. M (1996) Lysis of humant tumor cell lines by canine complement plus monoclonal antiganglioside antibodies or natural canine xenoantibodies. Cellular Immunology 167: 99-107.*
Cheung, N.V. et al., *Cancer Research* 45, pp. 2642-2649 (Jun. 1985).
Eisenberg, D. et al., *J. Mol. Biol.* 179, pp. 125-142 (1984).
Gagnon, Martin et al., *Expert Opinion* (2002).
Probstmeier et al., *Eur. J. Neuroscience*, vol. 11, pp. 2474-2488 (1999).
Saragovi, H. Uri et al., *Nature Biotechnology*, vol. 10, pp. 773-778 (Jul. 1992).
Sorkin, L.S., *Pain Medicine*, vol. 1, pp. 296-302 (2000).

* cited by examiner

*Primary Examiner*—Cecilia Tsang
*Assistant Examiner*—Maury Audet
(74) *Attorney, Agent, or Firm*—Klarquist Sparkman LLP

(57) ABSTRACT

The invention provides ligands of ganglioside GD2, including peptide ligands such as GGITNYNSALM; YCGGITNYNSACY; YCITNYNSCY; YCGGITNYNCY; YCTNYGVHCY; YCTNYGVCY; GGIANYNTS; YCGGIANYNCY; YCGGIANYNTSCY; and, YCIANYNTCY. GD2 ligands of the invention may for example be used to treat or diagnose diseases such as cancers in which cells express GD2, including neuroblastomas.

10 Claims, 12 Drawing Sheets

Figure 1

Figure 2A:
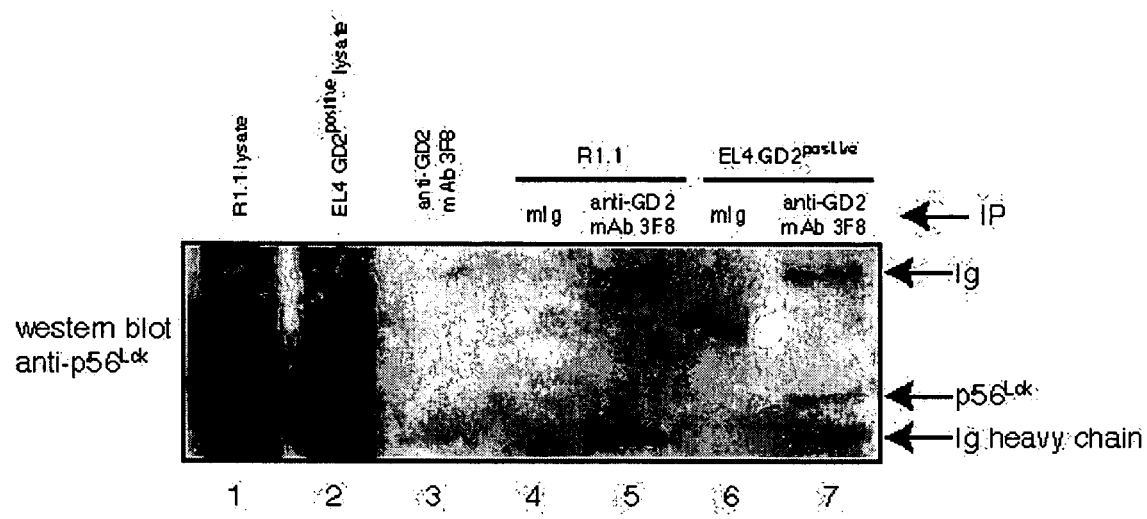

```
mgadgetvvl knmliginli llgsmikpse cqlevtterv qrqsveee gg ianynts ske    61
qpvvfnhvyn invpldnlcs sgleasaeqe vsaedetlae ymgqtsdhes qvtfthrinf    121
pkkacpcass aqvlqellsr iemlerevsv lrdqcnancc qesaatgqld yiphcsghgn    181
fsfescgcic negwfgkncs epycplgcss rgvcvdgqci cdseysgddc selrcptdcs    241
srglcvdgec vceepytged crelrcpgdc sgkgrcangt clceegyvge dcgqrqclna    301
csgrgqceeg lcvceegyqg pdcsavappe dlrvagisdr sielewdgpm avteyvisyq    361
ptalgglqlq qrvpgdwsgv titelepglt ynisvyavis nilslpitak vathlstpqg    421
lqfktitett vevqwepfsf sfdgweisfi pknneggvia qvpsdvtsfn qtglkpgeey    481
ivnvvalkeq arspptsasv stvidgptqi lvrdvsdtva fvewipprak vdfillkygl    541
vggeggrttf rlqpplsqys vqalrpgsry evsvsavrgt nesdsattqf tteidapknl    601
rvgsrtatsl dlewdnseae vqeykvvyst lageqyhevl vprgigpttr atltdlvpgt    661
eygvgisavm nsqqsvpatm narteldspr dlmvtasset sisliwtkas gpidhyritf    721
tpssgiasev tvpkdrtsyt ltdlepgaey iisvtaergr qqslestvda ftgfrpishl    781
hfshvtsssv nitwsdpspp adrlilnysp rdeeeemmev sldatkrhav lmglqpatey    841
ivnlvavhgt vtsepivgsi ttgidppkdi tisnvtkdsv mvswsppvas fdyyrvsyrp    901
tqvgrldssv vpntvtefti trlnpateye islnsvrgre eserictlvh tamdnpvdli    961
atnitpteal lqwkapvgev enyvivlthf avagetilvd gvseefrlvd llpsthytat   1021
myatngplts gtistnfstl ldppanltas evtrqsalis wqppraeien yvltykstdg   1081
srkelivdae dtwirlegll entdytvllq aaqdttwssi tstafttggr vfphpqdcaq   1141
hlmngdtlsg vypiflngel sqklqvycdm ttdgggwivf qrrqngqtdf frkwadyrvg   1201
fgnvedefwl gldnihrits qgryelrvdm rdgqeaafas ydrfsvedsr nlyklrigsy   1261
ngtagdslsy hqgrpfsted rdndvavtnc amsykgawwy knchrtnlng kygesrhsqg   1321
inwyhwkghe fsipfvemkm rpynhrlmag rkrqslqf
```

Figure 2
b.
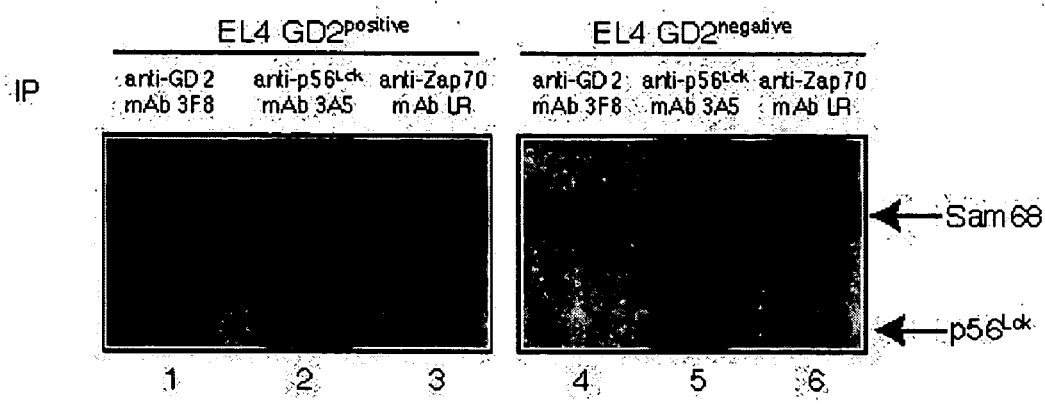
c.
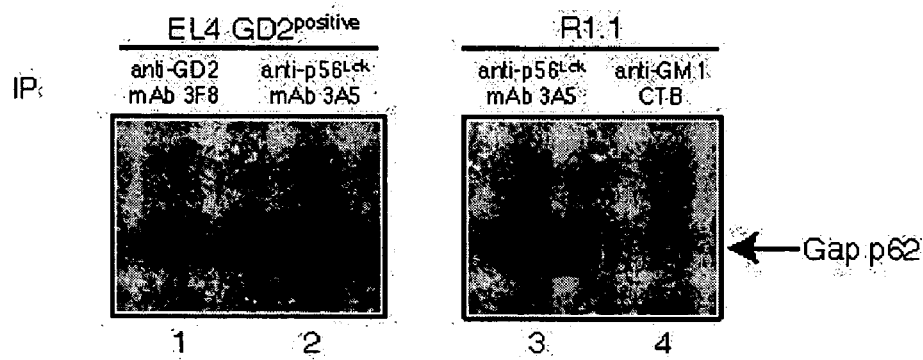

Figure 7.
a.
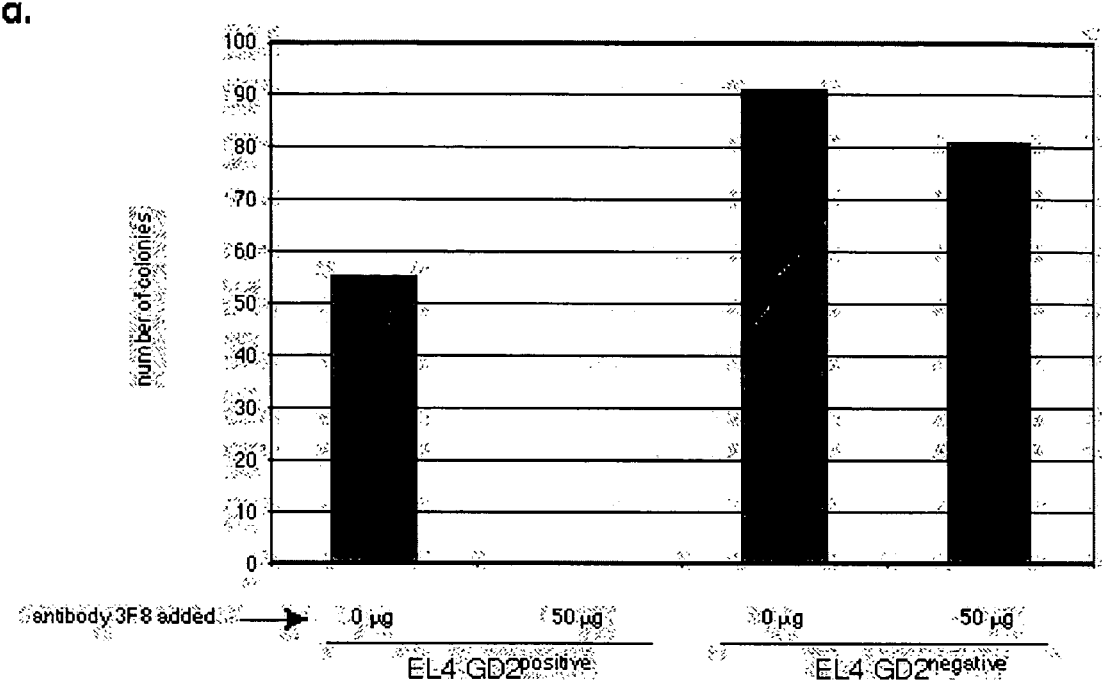
b.
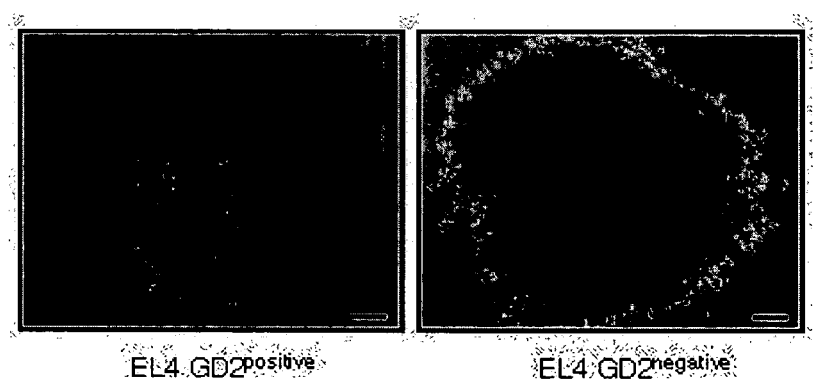

Figure 8.
a.
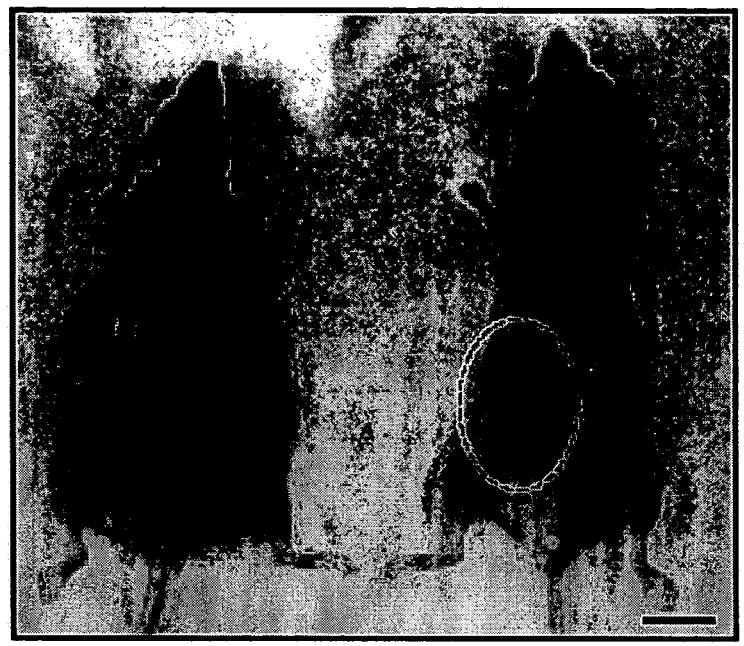
b.
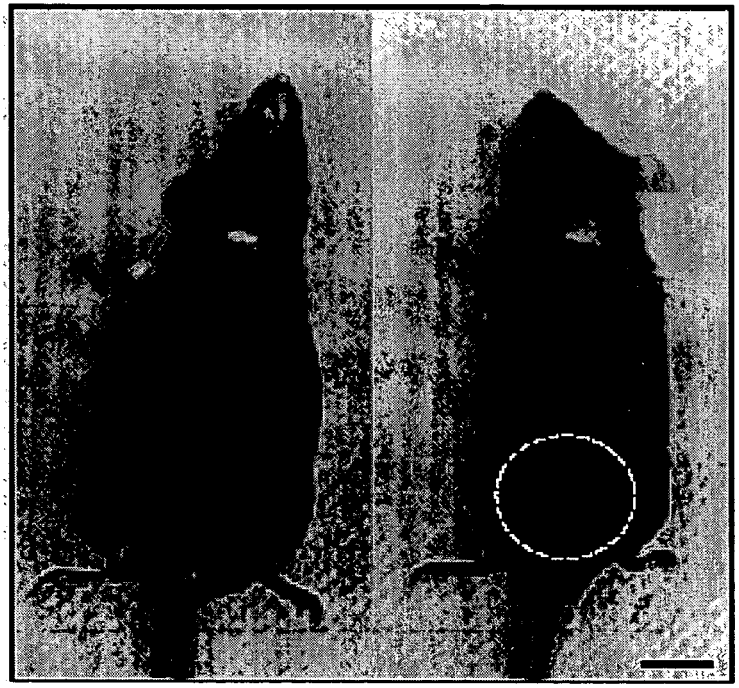

GD2 LIGANDS

REFERENCE TO RELATED APPLICATIONS

This is a § 371 U.S. National Stage of International Application No. PCT/CA2003/1001389, filed on Sep. 19, 2003, which was published in English under PCT Article 21(2), and which in turn claims the benefit of U.S. Provisional Application No. 60/412,492, filed Sep. 20, 2002, both of which are incorporated herein by reference.

FIELD OF THE INVENTION

The invention includes therapeutic compositions and methods, such as peptide cancer chemotherapeutic agents.

BACKGROUND OF THE INVENTION

Gangliosides are cell surface glycosphingolipids containing one or more sialic acid residues. It has been suggested that gangliosides may be localized within detergent-resistant cell membrane microdomains termed "rafts", which may provide the environment for some proteins to function by bringing together adapter molecules, modifiers, substrates, or cofactors that would be otherwise too distant or too dilute to form complexes and activate a signal cascade. However, little has been proposed regarding the possible mechanism of action of gangliosides in signal transduction.

Ganglioside GD2 is reportedly expressed at low levels in certain neuronal populations, but is highly prevalent in many types of tumors (neuroblastoma, melanoma, small cell carcinoma of the lung, gliomas, soft tissue sarcomas and B cell lymphoma).

The extracellular matrix component Tenascin-R was described recently as a natural ligand for GD2 (Probstmeier et al., 1999). However, relatively little is known about the biological function(s) of GD2 and the functional nature of its interaction with ligands such as Tenascin-R.

GD2 has been extensively studied as a tumor marker and is used clinically as a target for antibody-mediated therapy (e.g. anti-GD2 mAb 3F8) (Cheung et al., 1985). However, anti-GD2 mAb 3F8 applied therapeutically to patients causes acute and transient pain immediately after administration. Anti-GD2 mAb 3F8-based therapeutics have been suggested for use in a wide range of cancer therapeutics and diagnostics, including neuroblastoma and leptomeningeal cancer. For example, $^{131}$I-labeled anti-GD2 3F8 monoclonal antibody has been used in targeted radioimmunotherapy (dosed at 20 mCi/kg) in conjunction with immunotherapy with 400 mg/m2 unlabeled/unmodified 3F8. Similarly, granulocyte-macrophage colony-stimulating factor (GM-CSF) has been used in conjunction with anti-GD2 monoclonal antibody 3F8 in the treatment of patients with neuroblastoma.

SUMMARY OF THE INVENTION

In one aspect, the invention provides GD2 ligands of Formula I:

$$Z_1\text{-}X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}Z_2 \quad (I)$$

wherein
$X_1$ is absent or Y or an analogue thereof;
$X_2$ is absent or C or an analogue thereof;
$X_3$ is G or Y or an analogue thereof;
$X_4$ is G or C or Y or an analogue thereof;
$X_5$ is I or C or an analogue thereof;
$X_6$ is T or A or an analogue thereof;
$X_7$ is N or an analogue thereof;
$X_8$ is Y or an analogue thereof;
$X_9$ is N or G or an analogue thereof;
$X_{10}$ is S or C or V or T or an analogue thereof;
$X_{11}$ is A or C or Y or H or S or an analogue thereof;
$X_{12}$ is absent or L or C or Y or an analogue thereof;
$X_{13}$ is absent or M or Y or an analogue thereof;
$Z_1$ is an N-terminal group of the formula H2N—, RHN— or, RRN—;
$Z_2$ is a C-terminal group of the formula —C(O)OH, —C(O)R, —C(O)OR, —C(O)NHR, —C(O)NRR;
R at each occurrence is independently selected from ($C_1$-$C_6$)alkyl, ($C_1$-$C_6$)alkenyl, ($C_1$-$C_6$)alkynyl, substituted ($C_1$-$C_6$)alkyl, substituted ($C_1$-$C_6$)alkenyl, or substituted ($C_1$-$C_6$)alkynyl;
and wherein "-" is a covalent linkage.

In alternative embodiments, the invention provides substantially pure synthetic GD2 ligands or recombinant GD2 ligands having a domain of Formula II:

$$\text{-}X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-} \quad (II)$$

wherein
$X_1$ is absent or Y or an analogue thereof;
$X_2$ is absent or C or an analogue thereof;
$X_3$ is G or Y or an analogue thereof;
$X_4$ is G or C or Y or an analogue thereof;
$X_5$ is I or C or an analogue thereof;
$X_6$ is T or A or an analogue thereof;
$X_7$ is N or an analogue thereof;
$X_8$ is Y or an analogue thereof;
$X_9$ is N or G or an analogue thereof;
$X_{10}$ is S or C or V or T or an analogue thereof;
$X_{11}$ is A or C or Y or H or S or an analogue thereof;
$X_{12}$ is absent or L or C or Y or an analogue thereof;
$X_{13}$ is absent or M or Y or an analogue thereof;
and wherein "-" is a covalent linkage.

In one aspect, the invention provides recombinant proteins having domains of the invention, wherein the domain is capable of mediating binding of the recombinant protein to GD2. For example, recombinant T-cell receptors having the domains of the invention may be provided in transformed T-cell lines, such as cytotoxic T-cells (a "cytotoxic T lymphocyte" or "CTL" is an immune system cell that recognises epitopes presented by class I MHC molecules through its TCR.). Transformed T-cell lines of the invention may for example be used to treat diseases such as cancers having pathological tissues characterized by expression of GD2 (similar to an approach described in United States Patent Application 20020018783 A1, published in the name of Sadelain, M. et al. on Feb. 14, 2002, incorporated herein by reference).

The GD2 ligands of the invention may further comprise a cyclic linkage between any two of $X_1$ through $X_{13}$. In alternative embodiments, the GD2 ligands of the invention, or the domains of the invention, may be selected from the group consisting of: GGITNYNSALM; YCGGITNYNSACY; YCITNYNSCY; YCGGITNYNCY; YCTNYGVHCY; YCT-NYGVCY; GGIANYNTS; YCGGIANYNCY; YCG-GIANYNTSCY; and, YCIANYNTCY. In some embodiments, known GD2 ligands such as mAb 3F8 and tenascin-R are specifically excluded from the genus of claimed ligands in the present invention. However, in some embodiments, small molecule derivatives and analogs of known ligands (such as small peptides or peptidomimetics of the complementarity determining region of mAbs) are not excluded.

The invention also provides methods of treating a subject having a disease wherein disease cells express GD2, the method comprising administering to the subject an effective amount of the GD2 ligands of the invention. Also provided are methods of diagnosis of a disease wherein disease cells express GD2, comprising determining whether a cell from a subject binds to a GD2 ligand of the invention. The diagnostic and therapeutic methods of the invention may be carried out in vitro or in vivo.

In alternative embodiments, the GD2 ligands of the invention may be used with other therapeutic compounds, such as an effective amount of granulocyte-macrophage colony-stimulating factor. The invention provides commercial packages comprising the GD2 ligands of the invention, together with instructions for using the GD2 ligands to modulate GD2 activity or to detect cells expressing GD2.

Table 1 sets out the sequences of a number of alternative GD2 ligands or GD2 binding domains of the invention. Structure activity relationship (SAR) and deletion analysis demonstrate that some substitutions are allowed and that peptide cyclization enhances activity (peptides marked by * are inactive)

TABLE 1

| Alternative domains/peptides of the invention | | | | | | | | | | | | | |
|---|---|---|---|---|---|---|---|---|---|---|---|---|---|
| | | G | G | I | T | N | Y | N | S | A | L | M | |
| Y | C | G | G | I | T | N | Y | N | S | A | C | Y | |
| | | Y | C | I | T | N | Y | N | S | C | Y | | |
| Y | C | G | G | I | T | N | Y | N | C | Y | | | |
| | | | Y | C | T | N | Y | G | V | H | C | Y | * |
| | | | Y | C | T | N | Y | G | V | C | Y | | * |
| | | G | G | I | A | N | Y | N | T | S | | | * |
| Y | C | G | G | I | A | N | Y | N | C | Y | | | |
| Y | C | G | G | I | A | N | Y | N | T | S | C | Y | |
| | | Y | C | I | A | N | Y | N | T | C | Y | | |
| $X_1$ | $X_2$ | $X_3$ | $X_4$ | $X_5$ | $X_6$ | $X_7$ | $X_8$ | $X_9$ | $X_{10}$ | $X_{11}$ | $X_{12}$ | $X_{13}$ | |

The invention further provides commercial packages comprising a GD2 ligand, together with instructions for using the GD2 ligand, for example by administering the GD2 ligand to a patient in need of such treatment.

In alternative embodiments, the invention provides methods of screening to identify a GD2 ligand. For example, such screening methods may involve:

a) Administering a putative GD2 ligand (such as a polypeptide derived from Tenascin-R) to a system having a GD2 moiety and a $p56^{Lck}$ moiety available for association (such as a cell expressing GD2 and $p56^{Lck}$); and, b) Measuring an association between the GD2 and the $p56^{Lck}$ moieties in the system, for example by determining a kinase activity of the $p56^{Lck}$ moiety. In further alternative embodiments, the invention may include:

c) Measuring an association between the GD2 and the CD45 moieties in the system, for example by determining the phosphatase activity of the CD45 moiety.

In further alternative embodiments, the forgoing method further comprises:

b) Administering a putative GD2 ligand to a system having a GD2 moiety and a phosphatase such as CD45; and c) Measuring an association or functional relationship between GD2 and the phosphatase d) A competitive screening assay where test compounds (e.g. a combinatorial library) are used to displace any of the GD2 ligands described herein e) A competitive screening assay where any of the GD2 ligands described herein are used to displace test compounds In some embodiments, the putative GD2 ligand may for example comprise a polypeptide or a non-peptidic analog such as a peptidomimetic that displays the same pharmacophore or has similar side chain functional groups.

BRIEF DESCRIPTION OF THE DRAWINGS

FIG. 1 is the full-length protein sequence of Homo sapiens tenascin-R (restrictin, janusin), from GenBank Accession XP_040550, with a region identified in bold within a box that is identified in accordance with one aspect of the invention as a GD2 binding region. One aspect of the invention provides alternative tenascin-R proteins in which the GD2 binding region has been altered, for example to modulate the strength of the interaction between GD2 and the tenascin-R protein.

FIG. 2 shows data relating to the co-immunoprecipitation of GD2 and $p56^{Lck}$:

(a) R1.1 and EL4 $GD2^{positive}$ cell lysates were subjected to immunoprecipitation with anti-GD2 mAb 3F8 or control mouse IgG (mlg). Presence of $p56^{Lck}$ protein in the immunoprecipitates was evaluated by western blotting. $p56^{Lck}$ can be immunoprecipitated by mAb 3F8 in EL4 $GD2^{positive}$ cells (lane 7) but not in R1.1 cells (lane 5). Total cell lysates were used as a control for $p56^{Lck}$ detection (lane 1 and 2).

(b) and (c) R1.1, EL4 $GD2^{negative}$ and EL4 $GD2^{positive}$ cell lysates were subjected to immunoprecipitation with anti-GD2 mAb 3F8, GM1-binding cholera toxin B, anti-$p56^{Lck}$ mAb 3A5 and anti-Zap-70 mAb LR. Presence of $p56^{Lck}$ kinase activity in the immunoprecipitates was evaluated by in vitro kinase assay with the $p56^{Lck}$-specific substrates Sam68 and Gap p62. The data in FIG. 2(*b*) shows that $p56^{Lck}$ kinase activity can be immunoprecipitated by mAb 3F8 in EL4 $GD2^{positive}$ cells (lane 1) but not in EL4 $GD2^{negative}$ cells (lane 4). The data in FIG. 2(*c*) shows that $p56^{Lck}$ kinase activity can be immunoprecipitated by mAb 3F8 in EL4 $GD2^{positive}$ cells (lane 1) but by cholera toxin B in R1.1 cells (lane 4).

(d) R1.1 and EL4 $GD2^{positive}$ cell lysates were subjected to immunoprecipitation with anti-GD2 mAb 3F8, GM1-binding cholera toxin B and anti-$p56^{Lck}$ mAb 3A5. Presence of gangliosides GD2 and GM1 in the immunoprecipitates was evaluated by ELISA. Anti-$p56^{Lck}$ mAb 3A5 can immunoprecipitate GD2 from EL4 $GD2^{positive}$ cells, but can not immunoprecipitate GM1 from R1.1 cells. Shown are averages±SEM of one representative experiment. n=4 per experiment.

FIG. 3 shows the effect of gangliosides on the in vitro kinase activity of purified $p56^{Lck}$. The kinase activity of $p56^{Lck}$ was evaluated by measuring the incorporation of $^{32}PO_4$ in a peptidic p56$^{Lck}$ substrate over time, with or without GD2 or GM1. Presence of GD2, but not GM1, can positively alter the kinetics of p56$^{Lck}$ kinase activity. Activity standardized to untreated p56$^{Lck}$ at the 20 minute time point. Shown are averages of 3 to 5 assays±SEM.

FIG. 4 shows:

(a) the effect of GD2 ligands on p56$^{Lck}$ phosphorylation. Resting EL4 GD2$^{positive}$ cells were treated with mAb 3F8 (13 nM) or control mouse IgG (mIg) for the indicated times. After lysis, p56$^{Lck}$ protein was immunoprecipitated with anti-p56$^{Lck}$ mAb 3A5 and probed for phosphotyrosine (PY) by western blotting using biotinylated anti-phosphotyrosine mAb 4G10. Anti-GD2 mAb 3F8 can induce tyrosine phosphorylation of p56$^{Lck}$ within 5 minutes (lane 3) and sustain it for at least 30 minutes (lane 4).

(b) the effect of GD2 ligands on Zap-70 phosphorylation. Resting EL4 GD2positive cells were treated with mAb 3F8 (13 nM) or control mouse IgG (mIg) for the indicated times. After lysis, Zap-70 protein was immunoprecipitated with anti-Zap-70 mAb LR and probed for phosphotyrosine (PY) by western blotting using anti-phosphotyrosine mAb 4G10. Anti-GD2 mAb 3F8 can induce tyrosine phosphorylation of Zap-70 within 5 minutes (lane3).

(c) Effect of GD2 ligands on intracellular calcium concentrations. Resting EL4 GD2positive cells were treated with mAb 3F8 (13 nM), control mouse IgG (mIg) or the calcium ionophore A23187. Intracellular calcium concentration was evaluated over time by flow cytometry using the calcium-sensitive fluorophore Rhod-2 AM. mAb 3F8 can induce strong, sustainable calcium changes withing 5 minutes, while control mouse IgG has no effect. Addition of the p56Lck inhibitor PP1 partially abolished mAb 3F8's effects. Shown are averages of 4 independent assays ± SEM.

Figure 5:
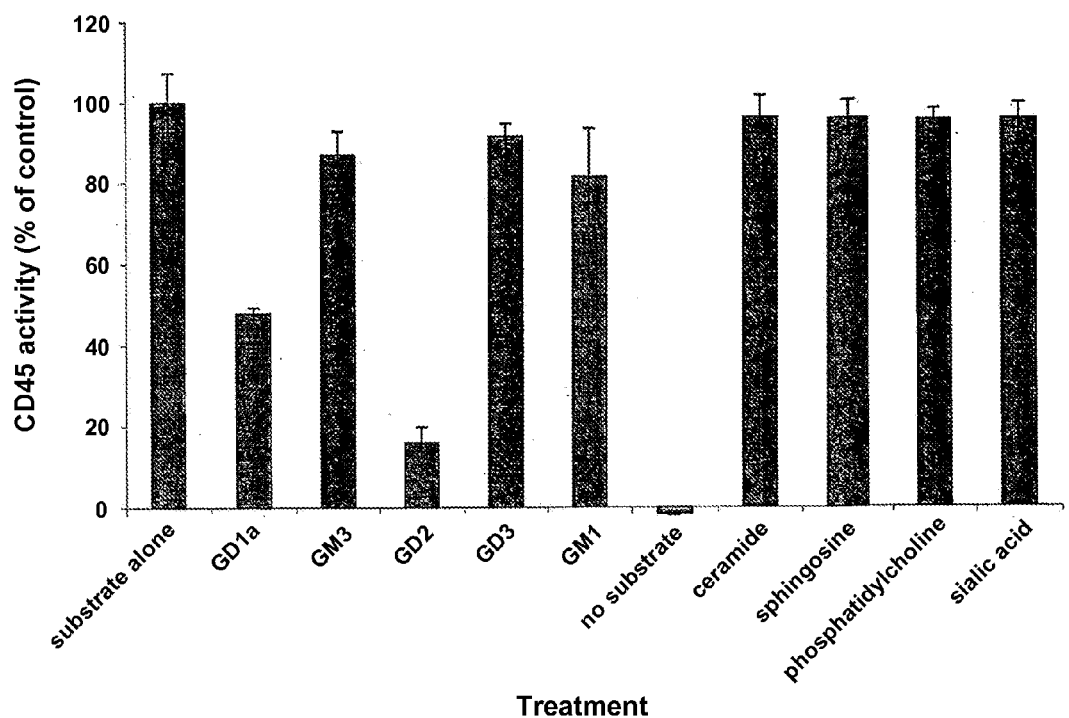

FIG. 5 shows the inhibitory effect of GD2 on in vitro CD45 phosphatase activity, particularly when using the pp60$^{Src}$ C-terminal phosphoregulatory sequence as a substrate. When co-incubated for 20 minutes, GD2 (but not other gangliosides) can drastically inhibit CD45 phosphatase activity, as measured by the colorimetric quantification of released free phosphate.

Figure 6:
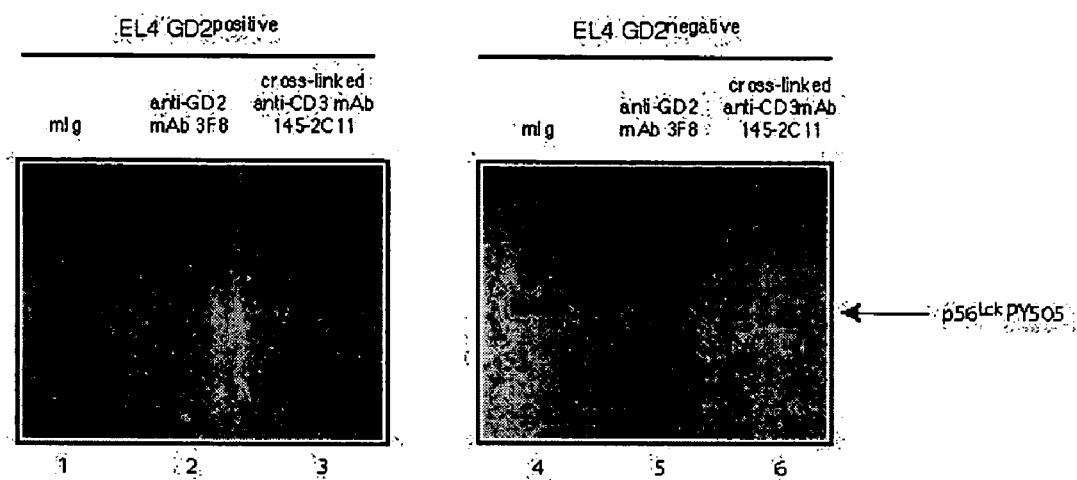

FIG. 6 shows the inhibitory effect of GD2 on ex vivo CD45 phosphatase activity, measured by the dephosphorylation of tyrosine 505 on p56$^{Lck}$. EL4 GD2$^{positive}$ and EL4 GD2$^{negative}$ cells were treated with control mIg, anti-GD2 antibody 3F8 or anti-CD3 antibody 145-2C11 cross-linked with anti-hamster antibody G94-56 for 20 minutes at 37° C. After lysis, p56$^{Lck}$ was immunoprecipitated with anti-p56$^{Lck}$ 3A5 coated beads and probed for phosphotyrosine at position 505 by western blotting with anti-PY505 antibody. EL4 GD2$^{positive}$ cells treated with anti-CD3 fail to induce dephosphorylation of p56$^{Lck}$ at tyrosine 505 (lane 3), while EL4 GD2$^{negative}$ cells show a marked dephosphorylation with the same treatment (lane 6), indicating that the presence of GD2 inhibits the CD45 phosphatase responsible for tyrosine 505 dephosphorylation. GD2 ligands such as anti-GD2 antibody 3F8, are able to relieve CD45 of its GD2-mediated inhibition (lane 2).

FIG. 7 shows data from soft-agar clonogenic assays. EL4 GD2$^{positive}$ and EL4 GD2$^{negative}$ cells were cultured in soft agar in the presence or absence of anti-GD2 antibody 3F8 (2 plates per sample).

(a) Total number of visible colonies. EL4 GD2$^{positive}$ cells show reduced colony formation compared to EL4 GD2$^{negative}$ cells. Anti-GD2 antibody 3F8 abolishes EL4 GD2$^{positive}$ cells growth but does not affect EL4 GD2$^{negative}$ cells.

(b) Typical EL4 GD2$^{positive}$ and EL4 GD2$^{negative}$ colonies. EL4 GD2$^{negative}$ colonies contain many more cells than EL4 GD2$^{positive}$ colonies. Bar=100 micrometers.

FIG. 8 shows data from tumorigenic assays. EL4 GD2$^{positive}$ and EL4 GD2$^{negative}$ cells were injected intraperitoneally in a) nude Balb/c and b) syngeneic C57BL/g mice. EL4 GD2$^{negative}$ injected animals (left) show important ascitic tumors, whereas EL4 GD2$^{positive}$ injected animals (right) show localized solid tumors (circled area). Bar=1 mm.

DETAILED DESCRIPTION OF THE INVENTION

In one aspect, the invention provides selective artificial ligands of GD2. In some embodiments, such ligands may be used to modulate ganglioside GD2 signal transduction selectively in the tissue where it is normally expressed, particularly in pathways that can be linked to tumorigenic growth or to nociceptive receptors. One aspect of the invention involves the identification of primary and tertiary structures in Tenascin-R that are critical for GD2 binding. In an alternative aspect, the invention demonstrates that a complementarity determining region of anti-GD2 mAb 3F8 is an analogue of Tenascin-R. Small peptide mimics of Tenascin-R and mimics of anti-GD2 mAb 3F8 have accordingly been designed and synthesized as selective ligands of GD2. Alternative ligands may be provided, based on the ligands of the invention, by protein mimicry and antibody mimicry techniques (Saragovi et al., 1992).

In an alternative aspect of the invention, it is demonstrated that GD2 (but not GM1) associates physically with p56$^{Lck}$ in vivo, in complexes that are stable to detergent lysis. It is shown that GD2 regulates signal transduction by enhancing p56$^{Lck}$ enzymatic activity in vitro and by enhancing in vivo phosphorylation of p56$^{Lck}$ and the p56$^{Lck}$ substrate Zap70. Accordingly, GD2 ligands of the invention may be used to cause p56$^{Lck}$-dependent fluxes in intracellular calcium in live cells, and thereby to modulate a variety of physiological or pathological cellular functions.

In an alternative aspect of the invention, it is demonstrated that GD2 (but not other gangliosides) can inhibit CD45 phosphatase activity in vitro and ex vivo. Accordingly, GD2 ligands of the invention may be used to antagonize the inhibitory action of GD2 on CD45 in live cells, and thereby to modulate a variety of physiological, immunological or pathological cellular functions.

In one aspect of the invention, expression of GD2 is shown to alter tumorigenicity in vitro and in vivo. As shown in the Examples, in EL4 clones that are otherwise phenotypically indistinguishable GD2$^{negative}$ than in GD2$^{positive}$ cells have equal doubling times, but soft agar colony growth is significantly more efficient in GD2$^{negative}$ cells. Further, addition of GD2 ligands in this assay causes the apoptotic death of GD2$^{positive}$ cells. GD2$^{negative}$ cells are also more tumorigenic in vivo. GD2$^{positive}$ cells injected intraperitoneally or subcutaneously in syngeneic mice only form solid tumors at the primary site, with little metastasis. In contrast, GD2$^{negative}$ cells can digest the peritoneal membrane, form viscous, muscin-like ascitic tumors, small solid tumor nodules, and are highly metastatic. Accordingly, in one aspect of the invention cells may be transformed so that they are GD2$^{positive}$, and the transformed GD2$^{positive}$ cells may be treated to GD2 ligands of the invention to mediate cell death, for example by an apoptotic pathway. For example, GD2$^{negative}$ cancer cells may be transformed by targeted gene therapy techniques, so that the cells become GD2$^{positive}$, and the transformed GD2$^{positive}$ cancer cells may be treated with a GD2 ligand of the invention.

In alternative aspects, GD2 ligands of the invention may be used to influence or modulate signal transduction in a biologically relevant manner in vitro and in vivo in the treatment of diseases such as cancer and in managing symptoms such as pain.

In one aspect, the invention provides compounds, such as GD2 ligands, that are purified, isolated or substantially pure. A compound is "substantially pure" when it is separated from the components that naturally accompany it. Typically, a compound is substantially pure when it is at least 60%, more generally 75% or over 90%, by weight, of the total material in a sample. Thus, for example, a polypeptide that is chemically synthesised or produced by recombinant technology will generally be substantially free from its naturally associated components. A nucleic acid molecule is substantially pure when it is not immediately contiguous with (i.e., covalently linked to) the coding sequences with which it is normally contiguous in the naturally occurring genome of the organism from which the DNA of the invention is derived. A substantially pure compound can be obtained, for example, by extraction from a natural source; by expression of a recombinant nucleic acid molecule encoding a polypeptide compound; or by chemical synthesis. Purity can be measured using any appropriate method such as column chromatography, gel electrophoresis, HPLC, etc.

The term "alkyl" refers to the radical of saturated aliphatic groups, including straight chain alkyl groups, branched-chain alkyl groups, cycloalkyl (alicyclic) groups, alkyl substituted cycloalkyl groups, and cycloalkyl substituted alkyl groups. Typical alkyl groups include, but are not limited to, methyl, ethyl, propyl, isopropyl, butyl, isobutyl, t-butyl, pentyl, isopentyl, hexyl, etc. The alkyl groups can be $(C_1-C_6)$alkyl, or $(C_1-C_3)$alkyl. A "substituted alkyl" has substituents replacing a hydrogen on one or more carbons of the hydrocarbon backbone. Such substituents can include, for example, halogen, hydroxyl, carbonyl (such as carboxyl, ketones (including alkylcarbonyl and arylcarbonyl groups), and esters (including alkyloxycarbonyl and aryloxycarbonyl groups)), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety. The moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The terms "alkenyl" and "alkynyl" refer to unsaturated aliphatic groups analogous in length and possible substitution to the alkyls described above, but that contain at least one double or triple bond respectively. An "alkenyl" is an unsaturated branched, straight chain, or cyclic hydrocarbon radical with at least one carbon-carbon double bond. The radical can be in either the cis or trans conformation about the double bond(s). Typical alkenyl groups include, but are not limited to, ethenyl, propenyl, isopropenyl, butenyl, isobutenyl, tert-butenyl, pentenyl, hexenyl, etc. An "alkynyl" is an unsaturated branched, straight chain, or cyclic hydrocarbon radical with at least one carbon-carbon triple bond. Typical alkynyl groups include, but are not limited to, ethynyl, propynyl, butynyl, isobutynyl, pentynyl, hexynyl, etc.

A "substantially identical" sequence is an amino acid or nucleotide sequence that differs from a reference sequence only by one or more conservative substitutions, as discussed herein, or by one or more non-conservative substitutions, deletion, or insertions located at positions of the sequence that do not destroy the biological function of the test compound. Such a sequence can be at least 60% or 75%, or more generally at least 80%, 85%, 90%, or 95%, or as much as 99% identical at the amino acid or nucleotide level to the sequence used for comparison. Sequence identity can be readily measured using publicly available sequence analysis software (e.g., Sequence Analysis Software Package of the Genetics Computer Group, University of Wisconsin Biotechnology Center, 1710 University Avenue, Madison, Wis. 53705, or BLAST software available from the National Library of Medicine). Examples of useful software include the programs, Pile-up and PrettyBox. Such software matches similar sequences by assigning degrees of homology to various substitutions, deletions, substitutions, and other modifications.

In alternative embodiments, GD2 ligands can be produced by substitution of either/or (i) side chains, (ii) backbone, or (iii) ionic interaction within a peptide. Additionally, structural or functional analogs can include 1) homologs of the peptidic GD2 ligands generated by peptidomimicry and 2) analogs where the sequence/structure of the GD2 ligands is introduced in a larger protein to convey GD2 binding to that protein.

In one aspect the invention provides nucleic acids that encode peptide compounds of the invention. Such nucleic acids may be introduced into cells for expression using standard recombinant techniques for stable or transient expression. Nucleic acid molecules of the invention may include any chain of two or more nucleotides including naturally occurring or non-naturally occurring nucleotides or nucleotide analogues.

Various genes and nucleic acid sequences of the invention may be recombinant sequences. The term "recombinant" means that something has been recombined, so that when made in reference to a nucleic acid construct the term refers to a molecule that is comprised of nucleic acid sequences that are joined together or produced by means of molecular biological techniques. The term "recombinant" when made in reference to a protein or a polypeptide refers to a protein or polypeptide molecule which is expressed using a recombinant nucleic acid construct created by means of molecular biological techniques. The term "recombinant" when made in reference to genetic composition refers to a gamete or progeny or cell or genome with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as 'recombinant' therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

In one aspect the invention provides antibodies that recognize compounds of the invention, and anti-idiotypic antibodies that in turn recognize such antibodies. The compounds of the invention can be used to prepare antibodies to GD2 ligands using standard techniques of preparation as, for example, described in Harlow and Lane (Antibodies: A Laboratory Manual, Cold Spring Harbor Laboratory, Cold Spring Harbor, N.Y., 1988), or known to those skilled in the art. Antibodies can be tailored to minimise adverse host immune response by, for example, using chimeric antibodies contain an antigen binding domain from one species and the Fc portion from another species, or by using antibodies made from hybridomas of the appropriate species.

Compounds of the invention can be prepared, for example, by replacing, deleting, or inserting an amino acid residue of a GD2 ligand or domain of the invention, with other conservatived amino acid residues, i.e., residues having similar physical, biological, or chemical properties, and screening for biological function. It is well known in the art that some modifications and changes can be made in the structure of a polypeptide without substantially altering the biological function of that peptide, to obtain a biologically equivalent polypeptide. The peptides, ligands and domains of the present invention also extend to biologically equivalent peptides, ligands and domains that differ from a portion of the sequence of novel ligands of the present invention by conservative amino acid substitutions. As used herein, the term "conserved amino acid substitutions" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

In some embodiments, conserved amino acid substitutions may be made where an amino acid residue is substituted for another having a similar hydrophilicity value (e.g., within a value of plus or minus 2.0), where the following may be an amino acid having a hydropathic index of about −1.6 such as Tyr (−1.3) or Pro (−1.6)s are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conserved amino acid substitutions may be made where an amino acid residue is substituted for another in the same class, where the amino acids are divided into non-polar, acidic, basic and neutral classes, as follows: non-polar Ala, Val, Leu, Ile, Phe, Trp, Pro, Met; acidic: Asp, Glu; basic: Lys, Arg, His; neutral: Gly, Ser, Thr, Cys, Asn, Gln, Tyr.

Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine(sarcosine), hydroxyproline, omithine, citrulline, t-butylalanine, t-butylglycine, N-methylisoleucine, phenylglycine, cyclohexylalanine, norleucine, norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, homoarginine, N-acetyl lysine, 2-amino butyric acid, 2-amino butyric acid, 2,4,-diamino butyric acid, p-aminophenylalanine, N-methylvaline, homocysteine, homoserine, cysteic acid, epsilon-amino hexanoic acid, delta-amino valeric acid, or 2,3-diaminobutyric acid.

In alternative embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (*J. Mol. Bio.* 179:125-142, 1984). Genetically encoded hydrophobic amino acids include Gly, Ala, Phe, Val, Leu, Ile, Pro, Met and Trp, and genetically encoded hydrophilic amino acids include Thr, His, Glu, Gln, Asp, Arg, Ser, and Lys. Non-genetically encoded hydrophobic amino acids include t-butylalanine, while non-genetically encoded hydrophilic amino acids include citrulline and homocysteine.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents such as —OH, —SH, —CN, —F, —Cl, —Br, —I, $—NO_2$, —NO, $—NH_2$, —NHR, —NRR, —C(O)R, —C(O)OH, —C(O)OR, $—C(O)NH_2$, —C(O)NHR, —C(O)NRR, etc., where R is independently $(C_1-C_6)$alkyl, substituted $(C_1-C_6)$alkyl, $(C_1-C_6)$alkenyl, substituted $(C_1-C_6)$alkenyl, $(C_1-C_6)$alkynyl, substituted $(C_1-C_6)$alkynyl, $(C_5-C_{20})$aryl, substituted $(C_5-C_{20})$aryl, $(C_6-C_{26})$alkaryl, substituted $(C_6-C_{26})$alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe, Tyr, and Tryp, while non-genetically encoded aromatic amino acids include phenylglycine, 2-napthylalanine, beta-2-thienylalanine, 1,2,3,4-tetrahydro-isoquinoline-3-carboxylic acid, 4-chlorophenylalanine, 2-fluorophenylalanine3-fluorophenylalanine, and 4-fluorophenylalanine.

An apolar amino acid is a hydrophobic amino acid with a side chain that is uncharged at physiological pH and which has bonds in which a pair of electrons shared in common by two atoms is generally held equally by each of the two atoms (i.e., the side chain is not polar). Genetically encoded apolar amino acids include Gly, Leu, Val, Ile, Ala, and Met, while non-genetically encoded apolar amino acids include cyclohexylalanine. Apolar amino acids can be further subdivided to include aliphatic amino acids, which is a hydrophobic amino acid having an aliphatic hydrocarbon side chain.

Genetically encoded aliphatic amino acids include Ala, Leu, Val, and Ile, while non-genetically encoded aliphatic amino acids include norleucine.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln, while non-genetically encoded polar amino acids include citrulline, N-acetyl lysine, and methionine sulfoxide.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His, while non-genetically encoded basic amino acids include the non-cyclic amino acids ornithine, 2,3,-diaminopropionic acid, 2,4-diaminobutyric acid, and homoarginine.

The above classifications are not absolute and an amino acid may be classified in more than one category. In addition, amino acids can be classified based on known behaviour and or characteristic chemical, physical, or biological properties based on specified assays or as compared with previously identified amino acids. Amino acids can also include bifunctional moieties having amino acid-like side chains.

Conservative changes can also include the substitution of a chemically derivatised moiety for a non-derivatised residue, by for example, reaction of a functional side group of an amino acid. Thus, these substitutions can include compounds whose free amino groups have been derivatised to amine hydrochlorides, p-toluene sulfonyl groups, carbobenzoxy groups, t-butyloxycarbonyl groups, chloroacetyl groups or formyl groups. Similarly, free carboxyl groups can be derivatized to form salts, methyl and ethyl esters or other types of esters or hydrazides, and side chains can be derivatized to form O-acyl or O-alkyl derivatives for free hydroxyl groups or N-im-benzylhistidine for the imidazole nitrogen of histidine. Peptide analogues also include amino acids that have been chemically altered, for example, by methylation, by amidation of the C-terminal amino acid by an alkylamine such as ethylamine, ethanolamine, or ethylene diamine, or acylation or methylation of an amino acid side chain (such as acylation of the epsilon amino group of lysine). Peptide analogues can also include replacement of the amide linkage in the peptide with a substituted amide (for example, groups of the formula —C(O)—NR, where R is $(C_1-C_6)$alkyl, $(C_1-C_6)$alkenyl, $(C_1-C_6)$alkynyl, substituted $(C_1-C_6)$alkyl, substituted $(C_1-C_6)$alkenyl, or substituted $(C_1-C_6)$alkynyl) or isostere of an amide linkage (for example, —CH$_2$NH—, —CH$_2$S, —CH$_2$CH$_2$—, —CH=CH— (cis and trans), —C(O)CH$_2$—, —CH(OH)CH$_2$—, or —CH$_2$SO—).

The GD2 ligands, peptides and domains of the invention may be covalently linked, for example, by polymerisation or conjugation, to form homopolymers or heteropolymers. Spacers and linkers, typically composed of small neutral molecules, such as amino acids that are uncharged under physiological conditions, can be used. Linkages can be achieved in a number of ways. For example, cysteine residues can be added at the peptide termini, and multiple peptides can be covalently bonded by controlled oxidation. Alternatively, heterobifunctional agents, such as disulfide/amide forming agents or thioether/amide forming agents can be used. The compound can also be linked to a lipid-containing molecule or peptide that can enhance a T cell response. The compound can also be constrained, for example, by having cyclic portions.

Peptides or peptide analogues can be synthesised by standard chemical techniques, for example, by automated synthesis using solution or solid phase synthesis methodology. Automated peptide synthesisers are commercially available and use techniques well known in the art. Peptides and peptide analogues can also be prepared using recombinant DNA technology using standard methods.

Compounds of the invention can be provided alone or in combination or conjugation with other compounds (for example, toxins, growth factors, anti-apoptotic agents, small molecules, peptides, or peptide analogues), in the presence of a liposome, an adjuvant, or any pharmaceutically acceptable carrier, in a form suitable for administration to humans. Conventional pharmaceutical practice may be employed to provide suitable formulations or compositions to administer the compounds to patients suffering from diseases such as cancer. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a compound according to the invention may be combined with more traditional therapies for the disease such as, for example, surgery or chemotherapy.

For therapeutic or prophylactic compositions, the compounds may be administered to an individual in an amount sufficient to induce the destruction of cells (such as cancer cells) or to stop or slow the destruction of cells (such as in neuroprotective treatments or treatment of pain). Amounts considered sufficient will vary according to the specific compound used, the mode of administration, the stage and severity of the disease, the age, sex, and health of the individual being treated, and concurrent treatments. As a general rule, however, dosages can range from about 1 microgram to about 100 mg per kg body weight of a patient for an initial dosage, with subsequent adjustments depending on the patient's response.

In the case of vaccine formulations, an immunogenically effective amount of a compound of the invention can be provided, alone or in combination with other compounds, with an adjuvant, for example, Freund's incomplete adjuvant or aluminum hydroxide. The compound may also be linked with a carrier molecule, such as bovine serum albumin or keyhole limpet hemocyanin to enhance immunogenicity.

In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

The following examples are intended to illustrate various embodiments and aspects of the invention, and do not limit the invention in any way.

EXAMPLES

Methods

Cells: EL4 murine lymphoma and R1.1 murine lymphoma were grown in RPMI 1640 medium (Life Technologies) supplemented with 5% fetal bovine serum, 2 mM glutamine, 10 mM Hepes and penicillin/streptomycin at 37° C. in 5% $CO_2$ humidified atmosphere. A GD2-negative mutant of EL4 was obtained after subcloning of EL4 cells resistant to culture with anti-GD2 mAb 3F8 and rabbit complement.

Flow cytometry: $10^5$ cells in 50 µl FACS buffer (PBS, 0.5% BSA, 0.05% $NaN_3$) were stained for 30 minutes on ice with the following ligands: for GD2, fluorescein isothiocyanate (FITC)-conjugated anti-GD2 mAb 3F8; for GM1, FITC-conjugated cholera toxin B subunit (Sigma); for GM2, rabbit anti-GM2 mAb NANA (Matreya) followed by FITC-conjugated anti-rabbit antibody (Sigma); for GD3, mouse anti-GD3 mAb (Pharmingen) followed by FITC conjugated anti-mouse antibody (Sigma). Cells were washed twice with FACS buffer and analyzed on a flow cytometer (Becton-Dickinson) using CellQuest software.

Detection of GD2 or GM1 by ELISA: 12.5 ng/well of ganglioside (GD2, Advanced Immunochemicals or GM1) were immobilized by drying onto PVC 96-well plates (Falcon), followed by blocking with PBS-0.5% BSA for one hour. Then, anti-GD2 mAb 3F8 or biotin-CTB were added for 10 minutes. The plate was washed three times with PBS-0.5% BSA and incubated 60 minutes with horseradish peroxidase (HRP)-conjugated anti-mouse antibody or HRP-conjugated-avidin. After three washes with PBS-0.5% BSA and two with PBS, the colorimetric substrate ABTS was added and the plate read at 414 nm on a Biorad 550 plate reader.

Co-immunoprecipitation of GD2 and $p56^{Lck}$: cells ($5 \times 10^6$ per sample) were washed in PBS, resuspended in 1 ml lysis buffer (150 mM NaCl, 10 mM sodium phosphate pH 7.2, 2 mM EDTA, 50 mM NaF, 1% CHAPS, 200 µM sodium orthovanadate, 1 mM PMSF, 100 µM leupeptin, 1 mM benzamidine, 300 nM aprotinin, 500 nM soybean trypsin inhibitor) and incubated 30 minutes at 4° C. Supernatants were collected from lysates after centrifugation (16000 g for 15 minutes at 4° C.). Immunoprecipitations were carried out overnight at 4° C. using 50 µl protein-G sepharose (Sigma) with either 5 µg of anti-GD2 mAb 3F8 or anti-$p56^{Lck}$ mAb 3A5 (Santa Cruz Biotechnology) or control IgG; or with 50 µl avidin-agarose (Sigma) and 5 µg of biotin-CTB which is specific for GM1 gangliosides. Immunoprecipitates were washed 5 times with 1 ml of cold lysis buffer containing decreasing concentration of CHAPS detergent and samples were extracted with reduced Laemmli buffer. Samples were then used for western blot analysis (see below), or lipids from the samples were isolated for ganglioside quantification by ELISA (see above).

Biochemical analysis: Western blotting: the immunoprecipitated samples were fractionated in SDS-PAGE and transferred to membranes, $p56^{Lck}$ immunoblotting was done using rabbit polyclonal anti-$p56^{Lck}$ antibody. Tyrosine phosphorylation of $p56^{Lck}$ and Zap70: cells ($5 \times 10^6$ per sample) were washed with PBS, resuspended in 5 ml protein-free hybridoma medium containing 0.2% BSA and allowed to rest for 60 minutes at 37° C. to lower baseline kinase activity. Then, 10 µg Anti-GD2 mAb 3F8 (13 nM concentration) or non-specific mouse IgG were added for 5 and 20 minutes. Samples were then washed in cold PBS, detergent solubilized in lysis buffer and immunoprecipitated using 5 µg of anti-$p56^{Lck}$ mAb 3A5 (Santa Cruz Biotechnology) or anti-Zap70 mAb LR (Santa Cruz Biotechnology). Samples were then analyzed by western blotting using anti-phosphotyrosine mAb 4G10. In vitro $p56^{Lck}$ kinase activity: $p56^{Lck}$ immunoprecipitates were incubated for 20 minutes at 37° C. with $p56^{Lck}$-specific substrates GAP p62 or Sam68 in a kinase reaction buffer (10 mM $MnCl_2$, 20 mM Tris-HCl pH 7.4, 2.5 µM ATP, 20 µCi [$\gamma$-$^{32}$P]ATP). The reaction was stopped by addition of reduced Laemmli buffer and boiling. Phosphorylation of $p56^{Lck}$ substrates was visualized and quantified by SDS-PAGE followed by analysis on a Storm 840 phosphorimager with ImageQuant software.

Effect of exogenous GD2 on $p56^{Lck}$ in vitro kinase assay: chromatographically purified $p56^{Lck}$ tyrosine kinase (Upstate Biotechnology) was incubated on ice for 10 minutes in kinase buffer (100 mM Tris-HCl, pH 7.2, 125 mM $MgCl_2$, 25 mM $MnCl_2$, 2 mM EGTA, 150 µM ATP, 0.25 mM sodium orthovanadate, 2 mM DTT) with or without ~20 fold molar excess of ganglioside and 10 µCi [$\gamma$-$^{32}$P]ATP. Then 10 µg of the Src kinase substrate peptide p34$^{cdc2}$(6-20) (Upstate Biotechnology) was added to the mix and incubated at room temperature for the times indicated, after which the reaction was stopped by addition of 100 µM iodoacetamide and by precipitation of proteins with final 10% TCA. The supernatant (containing the phosphorylated peptide substrate, not precipitated by TCA) was spotted on a P81 paper (Whatman) and washed three times with 0.75% phosphoric acid and once with acetone. The [$^{32}$P]-peptide content was quantified using a Storm 840 phosphorimager with ImageQuant software.

GD2 ligand design and synthesis: Peptides were modeled based on Tenascin-R sequence and on diversity within Tenascin family homologs. Peptides were synthesized with an Advanced Chemtech automatic synthesizer using solid-phase Fmoc chemistry. After cleavage from resin and side-chain deprotection, peptides containing terminal cysteines were subjected to cyclization by oxydation at 4° C. under $O_2$ in 50 mM ammonium bicarbonate, pH 8.5. Peptides were purified (>95%) by HPLC (Varian) using a C-18 preparative column (Phenomenex), and were verified by Mass Spectometry.

Assessment of peptide-GD2 interaction by competitive ELISA: ELISAs were as described above, except that peptides (50 µg/well, in PBS) were added to the wells for 1 hour before anti-GD2 mAb 3F8 or anti-GM1 cholera toxin-B. Selectivity of inhibition is controlled by lack of effect upon GM1-CTB interactions.

Intracellular calcium studies: cells ($1 \times 10^6$ per sample) were washed with Ringer's solution (155 mM NaCl, 4.5 mM KCl, 2 mM $CaCl_2$, 1 mM $MgCl_2$, 10 mM D-glucose, 5 mM HEPES) and resuspended in 1 ml Ringer's containing 10 µM $p56^{Lck}$ inhibitor PP1 (BioMol) or vehicle for 15 minutes at 37° C. Then 5 µM Rhod-2AM (Molecular Probes) was then added to the cells and incubated for 30 minutes at room temprature with mild agitation. Cells were washed once in Ringer's, resuspended in 1 ml Ringer's and incubated for 30 minutes, after which cells were stimulated with the indicated ganglioside ligands (or calcium ionophore A23187 as control) and analyzed over a 30 minute period for intracellular $Ca^{2+}$ using a flow cytometer (Becton-Dickinson).

Soft agar colony formation: single cell suspensions of EL4 $GD2^{negative}$ and EL4 $GD2^{positive}$ were plated (1500 cells/plate) with or without mAb 3F8 ( 50 µg/plate) in top layer medium (RPMI 1640 containing 0.35% agar, 15% fetal bovine serum, 2 mM glutamine, 10 mM Hepes and penicillin/streptomycin) on top of a preformed bottom layer (same as above except 0.5% agar) in 100 mm polystyrene dishes (Falcon) and grown until colonies are visible by eye. Colonies were counted in a predetermined area of the plates.

In vivo tumor studies: single cell suspensions of EL4 $GD2^{negative}$ and EL4 $GD2^{positive}$ in Hanks' balanced salt solution (Gibco) were injected intraperitoneally in nude Balb/c mice (Charles River) ($1 \times 10^6$ cells per animal). Animals were sacrificed and autopsied after 7 to 10 days, depending on tumor growth.

In vitro CD45 phosphatase assay: human recombinant CD45 enzyme (BioMol, 75 units/well) was preincubated in the absence (negative control) or presence of sodium orthovanadate (positive control) or various gangliosides (16.7 µM) for 20 minutes at room temperature in half-volume 96-well microtiter plates. A CD45-specific substrate ($pp60^{Src}$ C-terminal phosphoregulatory peptide, 200 µM) was then added for 20 minutes at 30° C., afterwhich the reaction was stopped and quantified with BioMol Green reagent. Plates were read at 620 nm with a Biorad 550 platew reader.

Ex vivo CD45 assay: single cell suspensions of EL4 $GD2^{negative}$ and EL4 $GD2^{positive}$ ($1 \times 10^7$ cells/ml per treatment) were incubated in the presence of 5 µg/ml of mIg (negative control), anti-GD2 antibody 3F8 or anti-CD3 antibody 145-2C11 (Pharmingen) cross-linked with anti-hamster G94-56 (Pharmingen) for 20 minutes at 37° C. in RPMI 1640 medium supplemented with 5% fetal bovine serum, 2 mM glutamine, 10 mM Hepes and penicillin/streptomycin. Cells were then washed and detergent lysed. $p56^{Lck}$ was then immunoprecipitated with anti-$p56^{Lck}$ antibody coated beads and probed for phosphotyrosine 505 by western blotting with anti-PY505 (Cell Signaling Technology).

Results

To study a specific physical association between $p56^{Lck}$ and gangliosides, a panel of cells was generated varying in expression of cell surface GD2, GM1, GM2 and GD3, as assessed by flow cytometry. The indicated cells (Table 2) express similar levels of $p56^{Lck}$ (data not shown).

control R1.1 cells, which are $GD2^{negative}$, no antibody co-precipitated $p56^{Lck}$, although $p56^{Lck}$ is expressed at high levels.

The presence and kinase activity of $p56^{Lck}$ in anti-GD2 immunoprecipitates were verified and quantified (FIGS. 2B and 2C). The indicated immunoprecipitations were done on EL4 $GD2^{positive}$ or EL4 $GD2^{negative}$ cells, followed by in vitro kinase assays using the specific $p56^{Lck}$ substrate Sam68. In EL4 $GD2^{positive}$ approximately 15% of the $p56^{Lck}$ activity was co-precipitated by anti-GD2 mAb 3F8 (FIG. 2B, lane 1), compared with anti-Lck mAb 3A5 (FIG. 2B, lane 2). In fact, anti-GD2 co-precipitation of the $p56^{Lck}$ activity was comparable to co-precipitation by antibodies against Zap70 (FIG. 2B, lane 3). This was in keeping with the fact that Zap70 and $p56^{Lck}$ are reportedly associated physically and functionally in vivo.

The specificity of these assays is validated in studies using EL4 $GD2^{negative}$ cells, where anti-GD2 mAb 3F8 did not co-precipitate a $p56^{Lck}$ activity (FIG. 2B, lane 4), while anti-Lck and anti-Zap70 antibodies did (FIG. 2B, lanes 5 and 6). Because $p56^{Lck}$ co-immunoprecipitations with anti-Zap70 antibodies were comparable in EL4 $GD2^{positive}$ and EL4 $GD2^{negative}$ cell lines (FIG. 2B, lanes 3 and 6), the data suggest that association of Zap70 and $p56^{Lck}$ can be GD2 independent.

Similar studies were done using EL4 $GD2^{positive}$ or R1.1 ($GD2^{negative}$) cells and assaying a $p56^{Lck}$ activity by in vitro kinase activity upon the selective substrate Gap62 (FIG. 2C). Again, anti-GD2 co-purified a $p56^{Lck}$ activity that corresponds to ~15% of the activity purified with anti-Lck mAb 3A5. In contrast, affinity isolation of GM1 with cholera toxin b subunit-coupled beads did not co-purify a $p56^{Lck}$ activity (FIG. 2C, lane 4), although R1.1 cells have high levels of GM1 and $p56^{Lck}$ (FIG. 2C, lane 3).

Figure 2D:
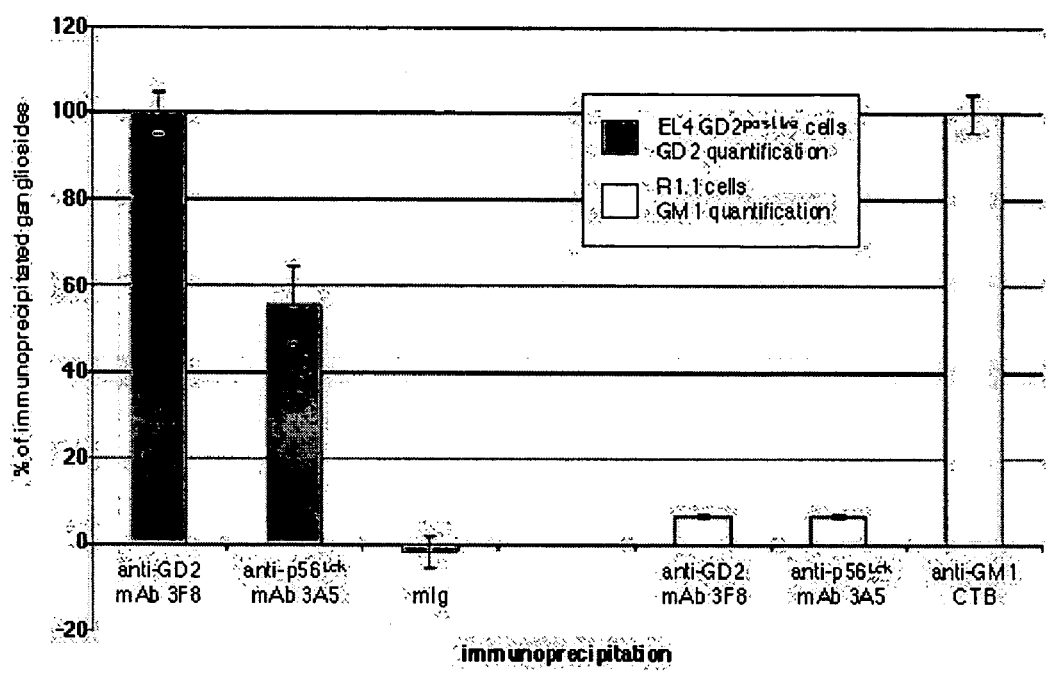

The converse experiment was performed where $p56^{Lck}$ was first immunoprecipitated with mAb 3A5 and then the presence of GD2 or GM1 were gauged by ELISA (FIG. 2D). Anti-$p56^{Lck}$ immunoprecipitates from EL4 $GD2^{positive}$ cells contained ~55% of the GD2 that could be isolated with anti-GD2 mAb 3F8. In specificity controls, anti-$p56^{Lck}$ immunoprecipitates from R1.1 cells did not co-precipitate the ganglioside GM1.

Functional Relevance of $p56^{Lck}$-$GD_2$ Association in the Absence of GD2 Ligands.

Figure 3:
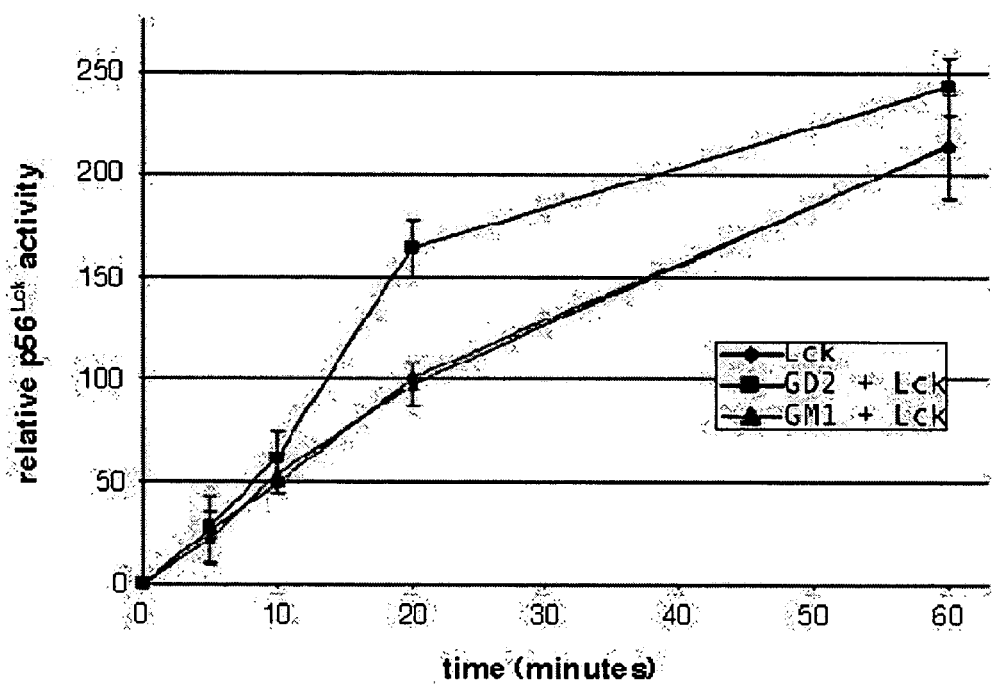

Subsequent experiments (FIG. 3) addressed in vitro whether there is a functional relevance to the stable and selective GD2-$p56^{Lck}$ association. Addition of exogenous GD2 to

TABLE 2

Surface ganglioside expression of cells studied as assessed by FACScan

| Cells | Source | Ganglioside profile | | | | $p56^{Lck}$ expression |
| --- | --- | --- | --- | --- | --- | --- |
| | | GM1 | GD2 | GD3 | GM2 | |
| EL4 $GD2^{positive}$ | lymphoma mouse C57/bl6n | Low | high | negative | negative | High |
| EL4 $GD2^{negative}$ | lymphoma mouse C57/bl6n | Low | negative | medium | negative | High |
| R1.1 | lymphoma mouse C58/J | High | low | negative | negative | High |

Specific and Stable Association of $p56^{Lck}$-GD2.

We performed anti-GD2 immunoprecipitations with mAb 3F8 followed by western blotting with anti-$p56^{Lck}$ antibodies (FIG. 2A). In EL4 $GD2^{positive}$ cells $p56^{Lck}$ was co-precipitated with mAb 3F8 but not with control mouse IgG. In purified $p56^{Lck}$ increased the kinetics of in vitro enzymatic activity from a $t_{1/2}$ of ~25 minutes to a $t_{1/2}$ of ~17 minutes, with a dramatic 70% increase in kinase activity at 20 minutes. However, the $v_{max}$ did not change, as the enzyme activity reaches a similar plateau with or without GD2 present. In control assays, $p56^{Lck}$ kinase activity was not altered upon addition of exogenous GM1 (FIG. 3), or addition of phosphatidylcholine or other lipids (data not shown).

Development of Artificial GD2 Ligands.

Small peptides (6-13 amino acids in length) were designed to span the primary sequence of the GD2 ligand Tenascin-R. Cyclization and other conformational constrains were introduced in these peptides to conformationally constrain them and to forcethem to adopt the β-turn structures desired.

These peptides (~100 were synthesized) were tested for inhibition of GD2-mAb 3F8 interactions in ELISA plates (Table 3). No competitor peptide added or control irrelevant peptide added were standardized as 100% binding. For simplicity, only some of the ~90 inactive peptides are shown.

Figure 4A:
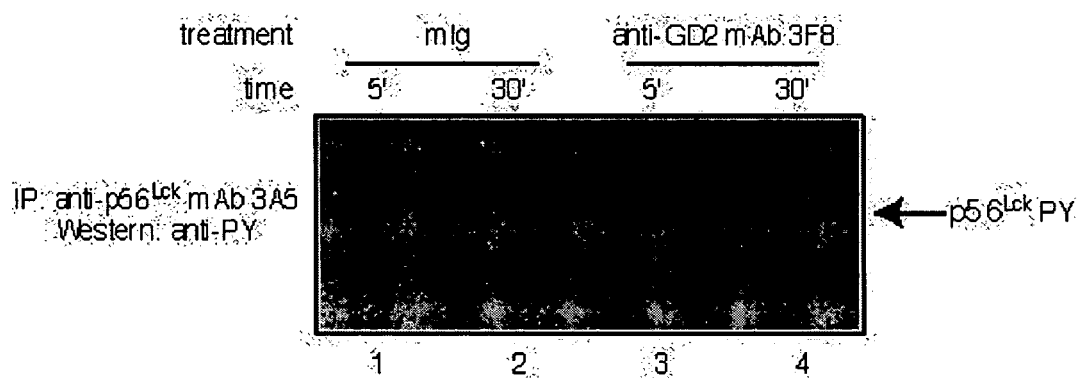

In various embodiments, peptide analogs that actively inhibit GD2-mAb 3F8 interactions span the sequence $NH_2$-Ile-Thr(Ala)-Asn-Tyr-Asn-COOH. In some embodiments, peptides of the invention may be in type IV (3:5 or 3:3) canonical β-turn configurations with a distance between the Cα1 to Cα4 atom varying between 4 and 7 Å, depending on whether Gly residues (underlined) are incorporated in the sequence. Additionally, a linear peptide of 11 amino acids (pep 51), which is unstructured in solution (data not shown) can also act as a competitive inhibitor.

the pTyr of $p56^{Lck}$ within 5 min in vivo (FIG. 4A, lanes 3 and 4). Control mouse IgG did not cause this effect (FIG. 4A, lanes 1 and 2).

Figure 4B:

Second, since the pTyr of $p56^{Lck}$ can lead either to activation or to inactivation of this kinase depending on which Tyr residue gets phosphorylated, the pTyr profile of Zap70 was studied in vivo because it is an adapter molecule downstream of and phosphorylated by activated $p56^{Lck}$. Zap70 is transiently pTyr upon engagement of cell-surface GD2 with mAb 3F8 as a ligand (FIG. 4B, lanes 3 and 4). This Zap70 pTyr presumably occurs via $p56^{Lck}$. Control mouse IgG did not cause Zap70 pTyr in EL4 $GD2^{positive}$ cells (FIG. 4B, lanes 1 and 2). In other specificity controls, treatment of EL4 $GD2^{negative}$ cells with GD2 ligands did not cause pTyr of $p56^{Lck}$ or Zap70 (data not shown) indicating that cell surface GD2 expression may be required for ligand engagement of GD2 and a subsequent effect downstream, in some embodiments.

Figure 4C:
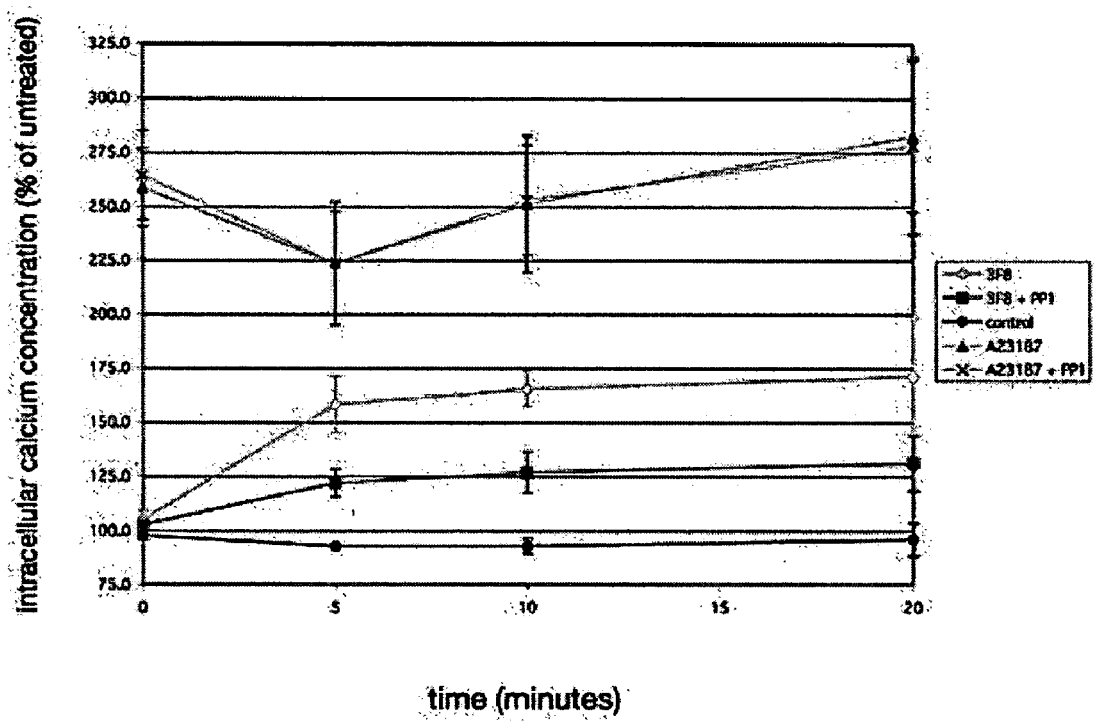

Third, intracellular $Ca^{++}$ concentrations were measured in live EL4 $GD2^{positive}$ cells after engagement of cell-surface GD2 with ligands (FIG. 4C). Flow cytometric analysis using the $Ca^{++}$ sensitive Rhod-2 fluorophore showed a rapid (~5 minutes) 1.6 fold increase of intracellular $Ca^{++}$ after mAb 3F8 binding, but not after binding by control mouse antibody or

TABLE 3

Selected peptide mimics . . .

| Peptides | Sequence | Conformation | % Inhibition of mAb 3F8-GD2 interactions |
|---|---|---|---|
| Pep 51 | <u>G G</u> I T N Y N S A L M | linear | 44.96 ± 1.57 |
| Pep 52 | C <u>G G</u> I T N Y N S A C | cyclic | 30.17 ± 2.69 |
| Pep 53 | C I T N Y N S C | cyclic | 24.74 ± 3.29 |
| Pep 54 | C <u>G G</u> I T N Y N C | cyclic | 40.34 ± 3.17 |
| Pep 55 | C T N Y G V H C | cyclic | 12.23 ± 4.41 |
| Pep 56 | C T N Y G V C | cyclic | 14.13 ± 5.43 |
| Pep 57 | G G I A N Y N T S | linear | 4.33 ± 5.23 |
| Pep 58 | C <u>G GI</u> A N Y N C | cyclic | 47.60 ± 4.26 |
| Pep 59 | C <u>G GI</u> A N Y N T S C | cyclic | 48.83 ± 5.01 |
| Pep 60 | C I A N Y N T C | cyclic | 30.94 ± 3.53 |

Inhibition of mAb 3F8 bindng to immobilized GD2 by peptides, measured by competitive ELISA. No peptide or control peptide treatments are standardized as 0% inhibition. No mAb 3F8 treatment is standardized as 100% inhibition. Average of 5 indepedant experiments, n=4 in each experiment. Mean±SEM.

Functional Relevance of GD2 Ligands in $p56^{Lck}$ Activation.

This example illustrates (i) whether engagement of cell surface GD2 with ligands causes the pTyr of $p56^{Lck}$ (FIG. 4A); (ii) whether engagement of cell surface GD2 with ligands leads to the pTyr of the downstream effector Zap70 (FIG. 4B); (iii) whether engagement of cell surface GD2 induces intracellular calcium fluxes (FIG. 4C).

First, engagement of cell surface GD2 in living EL4 $GD2^{positive}$ cells with the artificial GD2 ligand mAb 3F8 caused CTB (data not shown). The selective $p56^{Lck}$ kinase inhibitor PP1 (10 μM) markedly decreased mAb 3F8-induction of $Ca^{++}$ fluxes. This control suggests that activated $p56^{Lck}$ may be responsible for aspects of the GD2 signal transduction pathway leading to intracellular $Ca^{++}$ fluxes in some embodiments.

Functional Relevance of the Presence of GD2 on CD45 Activity.

Since the CD45 phosphatase is responsible for the activation of $p56^{Lck}$, the effect of GD2 on CD45 activity was investigated. First, the effect of GD2 was tested in vitro using human recombinant CD45 enzyme and $pp60^{Src}$ phosphoregulatory peptide as a substrate. As seen in FIG. 5, GD2 can drastically inhibit CD45 phosphatase activity (85% inhibition), while other gangliosides (GM1, GM2, GD3 and GM3)

had little influence on the enzymatic activity of CD45. Other than GD2, only GD1a showed significant inhibition (50%).

The inhibitory effect of GD2 on CD45 is also seen in live cells, as shown in FIG. 6. Here, EL4 GD2$^{positive}$ and EL4 GD2$^{negative}$ cells were stimulated using the well-documented T cell receptor cross-linking methodology, which typically results in activation of p56$^{Lck}$ following its dephosphorylation at tyrosine 505 by CD45. Interestingly, EL4GD2$^{positive}$ cells are resistant to activation (FIG. 6, lane 3), while the EL4 GD2$^{negative}$ cells (FIG. 7, lane 6) are readily activated upon T cell receptor cross-linking. This discrepancy can be attributed to the presence of GD2 in EL4 GD2$^{positive}$ cells which can block CD45-mediated activation of p56$^{Lck}$. Of interest is the fact that GD2 ligands, such as mAb 3F8, seem to be able to alleviate GD2 inhibition of CD45 and allow for T cell receptor activation as seen by dephosphorylation of tyrosine 505 on p56$^{Lck}$ (FIG. 6, lane 2).

Functional Relevance of GD2 and GD2 Ligands in Tumorigenic Growth.

To illustrate the effect of cell surface expression of GD2 on cancer cell growth and survival, EL4 GD2$^{positive}$ and EL4 GD2$^{negative}$ cells were grown in clonoenic (soft agar) assays (FIG. 7), or they were injected in vivo intraperitoneally (FIG. 8).

Colony formation assays in soft agar showed marked differences in growth dynamics for EL4 GD2$^{positive}$ and EL4 GD2$^{negative}$ cells. At day 10 of growth, the total number of EL4 GD2$^{positive}$ colonies per plate were lower by 50% compared to EL4 GD2$^{negative}$ colonies (FIG. 7a). Moreover the EL4 GD2$^{negative}$ colonies were much larger and contained more cells (FIG. 7b). This is striking because both cell lines have identical doubling times in liquid culture.

Addition of mAb 3F8 in the agar layer (where it putatively diffuses, engages and activates GD2-mediated signals) totally abolished EL4 GD2$^{positive}$ colony formation while having no consequences on the number and size of EL4 GD2$^{negative}$ colonies. This illustrates that the GD2 ligands of the invention may be used to treat GD2 positive cells to modulate growth, for example to treat cancer cells expressing GD2 to inhibit the growth of such cells or to kill the cells. In some embodiments, EL4 GD2$^{positive}$ cells die by apoptosis when GD2 is bound (data not shown), indicating that the presence of GD2 may in some embodiments allow the GD2 ligands of the invention to be used to induce apoptosis.

An evident difference is also observed when cells are grown in vivo. When injected intraperitoneally EL4 GD2$^{negative}$ cells mainly form aggressive and metastatic ascitic tumors and the peritoneal cavity contains mucin-like peptidoglycans. In contrast, EL4 GD2$^{positive}$ cells form localized, highly vascularized solid tumors attached to the peritoneal membrane (FIG. 8).

Conclusion

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

REFERENCES

The following documents are hereby incorporated by reference:

Cheung, N. K., Saarinen, U. M., Neely, J. E., Landmeier, B., Donovan, D., and Coccia, P. F. (1985). Monoclonal antibodies to a glycolipid antigen on human neuroblastoma cells, Cancer Research 45, 2642-9.

Eisenberg, D., Schwarz, E., Komaromy, M., Wall, R. (1984). Analysis of membrane and surface protein sequences with the hydrophobic moment plot, Journal of Molecular Biology 179, 125-42.

Gagnon, M., and Saragovi, H. U. (2002). Gangliosides: therapeutic agents or therapeutic targets?, Expert Opinion on Therapeutic Patents 12, 1215-1224.

Probstmeier, R., Michels, M., Franz, T., Chan, B. M., and Pesheva, P. (1999). Tenascin-R interferes with integrin-dependent oligodendrocyte precursor cell adhesion by a ganglioside-mediated signalling mechanism, European Journal of Neuroscience 11, 2474-88.

Saragovi, H. U., Greene, M. I., Chrusciel, R. A., and Kahn, M. (1992). Loops and secondary structure mimetics: development and applications in basic science and rational drug design, Bio/Technology 10, 773-8.

Sorkin, L. S. (2000). Antibody activation and immune reactions: potential linkage to pain and neuropathy, Pain Medicine 1, 296-302.

---

What is claimed is:

1. A substantially pure GD2 ligand, wherein said GD2 ligand comprises the peptide of GGITNYNSALM (SEQ ID NO: 3).

2. A substantially pure synthetic or recombinant GD2 ligand, wherein said GD2 ligand comprises the peptide of GGITNYNSALM (SEQ ID NO: 3).

3. A pharmaceutical composition comprising the GD2 ligand of claim 1, together with granulocyte-macrophage colony-stimulating factor.

4. A pharmaceutical composition comprising the GD2 ligand of claim 2, together with granulocyte-macrophage colony-stimulating factor.

5. A commercial package comprising the GD2 ligand of claim 1, together with instructions for using the GD2 ligand to modulate GD2 activity or detect cells expressing GD2.

6. A commercial package comprising the GD2 ligand of claim 2, together with instructions for using the GD2 ligand to modulate GD2 activity or detect cells expressing GD2.

7. The GD2 ligand of claim 2, wherein the GD2 ligand is a T-cell receptor.

8. The GD2 ligand of claim 7, wherein the T-cell receptor is expressed in a cytotoxic T cell line.

9. A method of treating a cell line, comprising transforming the cell line to provide transformed cells that express GD2, and treating the transformed cells with an effective amount of the GD2 ligand of claim 1.

10. A method of treating a cell line, comprising transforming the cell line to provide transformed cells that express GD2, and treating the transformed cells with an effective amount of the GD2 ligand of claim 2.

* * * * *

SEQUENCE LISTING

```
<160> NUMBER OF SEQ ID NOS: 23

<210> SEQ ID NO 1
<211> LENGTH: 13
<212> TYPE: PRT
<213> ORGANISM: Artificial
<220> FEATURE:
<223> OTHER INFORMATION: GD2 Ligand
<220> FEATURE:
<221> NAME/KEY: MISC_FEATURE
<222> LOCATION: (1)..(1)
```

```
<223> OTHER INFORMATION: Xaa = Absent or Tyr or an analogue thereof.
<220> FEATURE:
<221> NAME/KEY: MOD_RES
<222> LOCATION: (1)..(1)
<223> OTHER INFORMATION: The N-terminal group may be of the formula
      H2N-, RHN-, or, RRN-, wherein R at each occurence is independently
      selected from (C1-C6) alkyl, (C1-C6) alkenyl, (C1-C6) alkynyl,
      substituted (C1-C6) alkyl, substituted (C1-C6) alkenyl, or
      substituted (C1-C6) alkynyl.
<220> FEATURE:
<221> NAME/KEY: MISC_FEATURE
<222> LOCATION: (2)..(2)
<223> OTHER INFORMATION: Xaa = Absent or Cys or an analogue thereof.
<220> FEATURE:
<221> NAME/KEY: MISC_FEATURE
<222> LOCATION: (3)..(3)
<223> OTHER INFORMATION: Xaa = Gly or Tyr or an analogue thereof.
<220> FEATURE:
<221> NAME/KEY: MISC_FEATURE
<222> LOCATION: (4)..(4)
<223> OTHER INFORMATION: Xaa = Gly or Cys or Tyr or an analogue thereof.
<220> FEATURE:
<221> NAME/KEY: MISC_FEATURE
<222> LOCATION: (5)..(5)
<223> OTHER INFORMATION: Xaa = Ile or Cys or an analogue thereof.
<220> FEATURE:
<221> NAME/KEY: MISC_FEATURE
<222> LOCATION: (6)..(6)
<223> OTHER INFORMATION: Xaa = Thr or Ala or an analogue thereof.
<220> FEATURE:
<221> NAME/KEY: MISC_FEATURE
<222> LOCATION: (7)..(7)
<223> OTHER INFORMATION: Xaa = Asn or an analogue thereof.
<220> FEATURE:
<221> NAME/KEY: MISC_FEATURE
<222> LOCATION: (8)..(8)
<223> OTHER INFORMATION: Xaa = Tyr or an analogue thereof.
<220> FEATURE:
<221> NAME/KEY: MISC_FEATURE
<222> LOCATION: (9)..(9)
<223> OTHER INFORMATION: Xaa = Asn or Gly or an analogue thereof.
<220> FEATURE:
<221> NAME/KEY: MISC_FEATURE
<222> LOCATION: (10)..(10)
<223> OTHER INFORMATION: Xaa = Ser or Cys or Val or Thr or an analogue
      thereof.
<220> FEATURE:
<221> NAME/KEY: MISC_FEATURE
<222> LOCATION: (11)..(11)
<223> OTHER INFORMATION: Xaa = Ala or Cys or Tyr or His or Ser or an
      analogue thereof.
<220> FEATURE:
<221> NAME/KEY: MISC_FEATURE
<222> LOCATION: (12)..(12)
<223> OTHER INFORMATION: Xaa = absent or Leu or Cys or Tyr or an
      analogue thereof.
<220> FEATURE:
<221> NAME/KEY: MISC_FEATURE
<222> LOCATION: (13)..(13)
<223> OTHER INFORMATION: Xaa = absent or Met or Tyr or an analogue
      thereof.
<220> FEATURE:
<221> NAME/KEY: MOD_RES
<222> LOCATION: (13)..(13)
<223> OTHER INFORMATION: C-terminal grp is of the formula -C(O)OH,
      -C(O)R, -C(O)OR, -C(O)NHR, -C(O)NRR; wherein each R is
      independently selected from (C1-C6) alkyl, (C1-C6) alkenyl,
      (C1-C6) alkynyl, substituted (C1-C6) alkyl, substituted (C1-C6)
      alkenyl, or substituted (C1-C6) alkynyl.

<400> SEQUENCE: 1

Xaa Xaa Xaa Xaa Xaa Xaa Xaa Xaa Xaa Xaa Xaa Xaa Xaa
1               5                   10

<210> SEQ ID NO 2
<211> LENGTH: 13
<212> TYPE: PRT
```

```
<213> ORGANISM: Artificial
<220> FEATURE:
<223> OTHER INFORMATION: GD2 Ligand
<220> FEATURE:
<221> NAME/KEY: MISC_FEATURE
<222> LOCATION: (1)..(1)
<223> OTHER INFORMATION: Xaa = Absent or Tyr or an analogue thereof.
<220> FEATURE:
<221> NAME/KEY: MISC_FEATURE
<222> LOCATION: (2)..(2)
<223> OTHER INFORMATION: Xaa = Absent or Cys or an analogue thereof.
<220> FEATURE:
<221> NAME/KEY: MISC_FEATURE
<222> LOCATION: (3)..(3)
<223> OTHER INFORMATION: Xaa = Gly or Tyr or an analogue thereof.
<220> FEATURE:
<221> NAME/KEY: MISC_FEATURE
<222> LOCATION: (4)..(4)
<223> OTHER INFORMATION: Xaa = Gly or Cys or Tyr or an analogue thereof.
<220> FEATURE:
<221> NAME/KEY: MISC_FEATURE
<222> LOCATION: (5)..(5)
<223> OTHER INFORMATION: Xaa = Ile or Cys or an analogue thereof.
<220> FEATURE:
<221> NAME/KEY: MISC_FEATURE
<222> LOCATION: (6)..(6)
<223> OTHER INFORMATION: Xaa = Thr or Ala or an analogue thereof.
<220> FEATURE:
<221> NAME/KEY: MISC_FEATURE
<222> LOCATION: (7)..(7)
<223> OTHER INFORMATION: Xaa = Asn or an analogue thereof.
<220> FEATURE:
<221> NAME/KEY: MISC_FEATURE
<222> LOCATION: (8)..(8)
<223> OTHER INFORMATION: Xaa = Tyr or an analogue thereof.
<220> FEATURE:
<221> NAME/KEY: MISC_FEATURE
<222> LOCATION: (9)..(9)
<223> OTHER INFORMATION: Xaa = Asn or Gly or an analogue thereof.
<220> FEATURE:
<221> NAME/KEY: MISC_FEATURE
<222> LOCATION: (10)..(10)
<223> OTHER INFORMATION: Xaa = Ser or Cys or Val or Thr or an analogue
      thereof.
<220> FEATURE:
<221> NAME/KEY: MISC_FEATURE
<222> LOCATION: (11)..(11)
<223> OTHER INFORMATION: Xaa = Ala or Cys or Tyr or His or Ser or an
      analogue thereof.
<220> FEATURE:
<221> NAME/KEY: MISC_FEATURE
<222> LOCATION: (12)..(12)
<223> OTHER INFORMATION: Xaa = Absent or Leu or Cys or Tyr or an
      analogue thereof.
<220> FEATURE:
<221> NAME/KEY: MISC_FEATURE
<222> LOCATION: (13)..(13)
<223> OTHER INFORMATION: Xaa = Absent or Met or Tyr or an analogue
      thereof.

<400> SEQUENCE: 2

Xaa Xaa Xaa Xaa Xaa Xaa Xaa Xaa Xaa Xaa Xaa Xaa Xaa
1               5                   10

<210> SEQ ID NO 3
<211> LENGTH: 11
<212> TYPE: PRT
<213> ORGANISM: Artificial
<220> FEATURE:
<223> OTHER INFORMATION: GD2 Ligand

<400> SEQUENCE: 3

Gly Gly Ile Thr Asn Tyr Asn Ser Ala Leu Met
1               5                   10
```

```
<210> SEQ ID NO 4
<211> LENGTH: 13
<212> TYPE: PRT
<213> ORGANISM: Artificial
<220> FEATURE:
<223> OTHER INFORMATION: GD2 Ligand

<400> SEQUENCE: 4

Tyr Cys Gly Gly Ile Thr Asn Tyr Asn Ser Ala Cys Tyr
1               5                   10

<210> SEQ ID NO 5
<211> LENGTH: 10
<212> TYPE: PRT
<213> ORGANISM: Artificial
<220> FEATURE:
<223> OTHER INFORMATION: GD2 Ligand

<400> SEQUENCE: 5

Tyr Cys Ile Thr Asn Tyr Asn Ser Cys Tyr
1               5                   10

<210> SEQ ID NO 6
<211> LENGTH: 11
<212> TYPE: PRT
<213> ORGANISM: Artificial
<220> FEATURE:
<223> OTHER INFORMATION: GD2 Ligand

<400> SEQUENCE: 6

Tyr Cys Gly Gly Ile Thr Asn Tyr Asn Cys Tyr
1               5                   10

<210> SEQ ID NO 7
<211> LENGTH: 10
<212> TYPE: PRT
<213> ORGANISM: Artificial
<220> FEATURE:
<223> OTHER INFORMATION: GD2 Ligand

<400> SEQUENCE: 7

Tyr Cys Thr Asn Tyr Gly Val His Cys Tyr
1               5                   10

<210> SEQ ID NO 8
<211> LENGTH: 9
<212> TYPE: PRT
<213> ORGANISM: Artificial
<220> FEATURE:
<223> OTHER INFORMATION: GD2 Ligand

<400> SEQUENCE: 8

Tyr Cys Thr Asn Tyr Gly Val Cys Tyr
1               5

<210> SEQ ID NO 9
<211> LENGTH: 9
<212> TYPE: PRT
<213> ORGANISM: Artificial
<220> FEATURE:
<223> OTHER INFORMATION: GD2 Ligand

<400> SEQUENCE: 9

Gly Gly Ile Ala Asn Tyr Asn Thr Ser
1               5

<210> SEQ ID NO 10
```

```
<211> LENGTH: 11
<212> TYPE: PRT
<213> ORGANISM: Artificial
<220> FEATURE:
<223> OTHER INFORMATION: GD2 Ligand

<400> SEQUENCE: 10

Tyr Cys Gly Gly Ile Ala Asn Tyr Asn Cys Tyr
1               5                   10

<210> SEQ ID NO 11
<211> LENGTH: 13
<212> TYPE: PRT
<213> ORGANISM: Artificial
<220> FEATURE:
<223> OTHER INFORMATION: GD2 Ligand

<400> SEQUENCE: 11

Tyr Cys Gly Gly Ile Ala Asn Tyr Asn Thr Ser Cys Tyr
1               5                   10

<210> SEQ ID NO 12
<211> LENGTH: 10
<212> TYPE: PRT
<213> ORGANISM: Artificial
<220> FEATURE:
<223> OTHER INFORMATION: GD2 Ligand

<400> SEQUENCE: 12

Tyr Cys Ile Ala Asn Tyr Asn Thr Cys Tyr
1               5                   10

<210> SEQ ID NO 13
<211> LENGTH: 5
<212> TYPE: PRT
<213> ORGANISM: Artificial
<220> FEATURE:
<223> OTHER INFORMATION: Spanning sequence for peptide analogs that
      actively inhibit GD2-mAb 3F8 interactions.

<400> SEQUENCE: 13

Ile Thr Asn Tyr Asn
1               5

<210> SEQ ID NO 14
<211> LENGTH: 5
<212> TYPE: PRT
<213> ORGANISM: Artificial
<220> FEATURE:
<223> OTHER INFORMATION: Spanning sequence for peptide analogs that
      actively inhibit GD2-mAb 3F8 interactions.

<400> SEQUENCE: 14

Ile Ala Asn Tyr Asn
1               5

<210> SEQ ID NO 15
<211> LENGTH: 11
<212> TYPE: PRT
<213> ORGANISM: Artificial
<220> FEATURE:
<223> OTHER INFORMATION: Peptide Mimic
<220> FEATURE:
<221> NAME/KEY: MISC_FEATURE
<222> LOCATION: (1)..(11)
<223> OTHER INFORMATION: Peptide is cyclic.

<400> SEQUENCE: 15
```

```
Cys Gly Gly Ile Thr Asn Tyr Asn Ser Ala Cys
1               5                   10
```

<210> SEQ ID NO 16
<211> LENGTH: 8
<212> TYPE: PRT
<213> ORGANISM: Artificial
<220> FEATURE:
<223> OTHER INFORMATION: Peptide Mimic
<220> FEATURE:
<221> NAME/KEY: MISC_FEATURE
<222> LOCATION: (1)..(8)
<223> OTHER INFORMATION: Peptide is cyclic.

<400> SEQUENCE: 16

```
Cys Ile Thr Asn Tyr Asn Ser Cys
1               5
```

<210> SEQ ID NO 17
<211> LENGTH: 9
<212> TYPE: PRT
<213> ORGANISM: Artificial
<220> FEATURE:
<223> OTHER INFORMATION: Peptide Mimic
<220> FEATURE:
<221> NAME/KEY: MISC_FEATURE
<222> LOCATION: (1)..(9)
<223> OTHER INFORMATION: Peptide is cyclic.

<400> SEQUENCE: 17

```
Cys Gly Gly Ile Thr Asn Tyr Asn Cys
1               5
```

<210> SEQ ID NO 18
<211> LENGTH: 8
<212> TYPE: PRT
<213> ORGANISM: Artificial
<220> FEATURE:
<223> OTHER INFORMATION: Peptide Mimic
<220> FEATURE:
<221> NAME/KEY: MISC_FEATURE
<222> LOCATION: (1)..(8)
<223> OTHER INFORMATION: Peptide is cyclic.

<400> SEQUENCE: 18

```
Cys Thr Asn Tyr Gly Val His Cys
1               5
```

<210> SEQ ID NO 19
<211> LENGTH: 7
<212> TYPE: PRT
<213> ORGANISM: Artificial
<220> FEATURE:
<223> OTHER INFORMATION: Peptide Mimic
<220> FEATURE:
<221> NAME/KEY: MISC_FEATURE
<222> LOCATION: (1)..(7)
<223> OTHER INFORMATION: Peptide is cyclic.

<400> SEQUENCE: 19

```
Cys Thr Asn Tyr Gly Val Cys
1               5
```

<210> SEQ ID NO 20
<211> LENGTH: 9
<212> TYPE: PRT
<213> ORGANISM: Artificial
<220> FEATURE:
<223> OTHER INFORMATION: Peptide Mimic
<220> FEATURE:

```
<221> NAME/KEY: MISC_FEATURE
<222> LOCATION: (1)..(9)
<223> OTHER INFORMATION: Peptide is cyclic.

<400> SEQUENCE: 20

Cys Gly Gly Ile Ala Asn Tyr Asn Cys
1               5

<210> SEQ ID NO 21
<211> LENGTH: 11
<212> TYPE: PRT
<213> ORGANISM: Artificial
<220> FEATURE:
<223> OTHER INFORMATION: Peptide Mimic

<400> SEQUENCE: 21

Cys Gly Gly Ile Ala Asn Tyr Asn Thr Ser Cys
1               5                   10

<210> SEQ ID NO 22
<211> LENGTH: 8
<212> TYPE: PRT
<213> ORGANISM: Artificial
<220> FEATURE:
<223> OTHER INFORMATION: Peptide mimic.
<220> FEATURE:
<221> NAME/KEY: MISC_FEATURE
<222> LOCATION: (1)..(8)
<223> OTHER INFORMATION: Peptide is cyclic.

<400> SEQUENCE: 22

Cys Ile Ala Asn Tyr Asn Thr Cys
1               5

<210> SEQ ID NO 23
<211> LENGTH: 1358
<212> TYPE: PRT
<213> ORGANISM: Homo sapiens

<400> SEQUENCE: 23

Met Gly Ala Asp Gly Glu Thr Val Val Leu Lys Asn Met Leu Ile Gly
1               5                   10                  15

Ile Asn Leu Ile Leu Leu Gly Ser Met Ile Lys Pro Ser Glu Cys Gln
                20                  25                  30

Leu Glu Val Thr Thr Glu Arg Val Gln Arg Gln Ser Val Glu Glu Glu
            35                  40                  45

Gly Gly Ile Ala Asn Tyr Asn Thr Ser Lys Glu Gln Pro Val Val
        50                  55                  60

Phe Asn His Val Tyr Asn Ile Asn Val Pro Leu Asp Asn Leu Cys Ser
65                  70                  75                  80

Ser Gly Leu Glu Ala Ser Ala Glu Gln Glu Val Ser Ala Glu Asp Glu
                85                  90                  95

Thr Leu Ala Glu Tyr Met Gly Gln Thr Ser Asp His Glu Ser Gln Val
            100                 105                 110

Thr Phe Thr His Arg Ile Asn Phe Pro Lys Lys Ala Cys Pro Cys Ala
        115                 120                 125

Ser Ser Ala Gln Val Leu Gln Glu Leu Leu Ser Arg Ile Glu Met Leu
    130                 135                 140

Glu Arg Glu Val Ser Val Leu Arg Asp Gln Cys Asn Ala Asn Cys Cys
145                 150                 155                 160

Gln Glu Ser Ala Ala Thr Gly Gln Leu Asp Tyr Ile Pro His Cys Ser
                165                 170                 175
```

-continued

```
Gly His Gly Asn Phe Ser Phe Glu Ser Cys Gly Cys Ile Cys Asn Glu
            180                 185                 190

Gly Trp Phe Gly Lys Asn Cys Ser Glu Pro Tyr Cys Pro Leu Gly Cys
        195                 200                 205

Ser Ser Arg Gly Val Cys Val Asp Gly Gln Cys Ile Cys Asp Ser Glu
    210                 215                 220

Tyr Ser Gly Asp Asp Cys Ser Glu Leu Arg Cys Pro Thr Asp Cys Ser
225                 230                 235                 240

Ser Arg Gly Leu Cys Val Asp Gly Glu Cys Val Cys Glu Glu Pro Tyr
                245                 250                 255

Thr Gly Glu Asp Cys Arg Glu Leu Arg Cys Pro Gly Asp Cys Ser Gly
            260                 265                 270

Lys Gly Arg Cys Ala Asn Gly Thr Cys Leu Cys Glu Glu Gly Tyr Val
        275                 280                 285

Gly Glu Asp Cys Gly Gln Arg Gln Cys Leu Asn Ala Cys Ser Gly Arg
    290                 295                 300

Gly Gln Cys Glu Glu Gly Leu Cys Val Cys Glu Glu Gly Tyr Gln Gly
305                 310                 315                 320

Pro Asp Cys Ser Ala Val Ala Pro Pro Glu Asp Leu Arg Val Ala Gly
                325                 330                 335

Ile Ser Asp Arg Ser Ile Glu Leu Glu Trp Asp Gly Pro Met Ala Val
            340                 345                 350

Thr Glu Tyr Val Ile Ser Tyr Gln Pro Thr Ala Leu Gly Gly Leu Gln
        355                 360                 365

Leu Gln Gln Arg Val Pro Gly Asp Trp Ser Gly Val Thr Ile Thr Glu
    370                 375                 380

Leu Glu Pro Gly Leu Thr Tyr Asn Ile Ser Val Tyr Ala Val Ile Ser
385                 390                 395                 400

Asn Ile Leu Ser Leu Pro Ile Thr Ala Lys Val Ala Thr His Leu Ser
                405                 410                 415

Thr Pro Gln Gly Leu Gln Phe Lys Thr Ile Thr Glu Thr Thr Val Glu
            420                 425                 430

Val Gln Trp Glu Pro Phe Ser Phe Ser Phe Asp Gly Trp Glu Ile Ser
        435                 440                 445

Phe Ile Pro Lys Asn Asn Glu Gly Gly Val Ile Ala Gln Val Pro Ser
    450                 455                 460

Asp Val Thr Ser Phe Asn Gln Thr Gly Leu Lys Pro Gly Glu Glu Tyr
465                 470                 475                 480

Ile Val Asn Val Val Ala Leu Lys Glu Gln Ala Arg Ser Pro Pro Thr
                485                 490                 495

Ser Ala Ser Val Ser Thr Val Ile Asp Gly Pro Thr Gln Ile Leu Val
            500                 505                 510

Arg Asp Val Ser Asp Thr Val Ala Phe Val Glu Trp Ile Pro Pro Arg
        515                 520                 525

Ala Lys Val Asp Phe Ile Leu Leu Lys Tyr Gly Leu Val Gly Gly Glu
    530                 535                 540

Gly Gly Arg Thr Thr Phe Arg Leu Gln Pro Pro Leu Ser Gln Tyr Ser
545                 550                 555                 560

Val Gln Ala Leu Arg Pro Gly Ser Arg Tyr Glu Val Ser Val Ser Ala
                565                 570                 575

Val Arg Gly Thr Asn Glu Ser Asp Ser Ala Thr Thr Gln Phe Thr Thr
            580                 585                 590
```

-continued

```
Glu Ile Asp Ala Pro Lys Asn Leu Arg Val Gly Ser Arg Thr Ala Thr
            595                 600                 605

Ser Leu Asp Leu Glu Trp Asp Asn Ser Glu Ala Glu Val Gln Glu Tyr
    610                 615                 620

Lys Val Val Tyr Ser Thr Leu Ala Gly Glu Gln Tyr His Glu Val Leu
625                 630                 635                 640

Val Pro Arg Gly Ile Gly Pro Thr Thr Arg Ala Thr Leu Thr Asp Leu
                645                 650                 655

Val Pro Gly Thr Glu Tyr Gly Val Gly Ile Ser Ala Val Met Asn Ser
            660                 665                 670

Gln Gln Ser Val Pro Ala Thr Met Asn Ala Arg Thr Glu Leu Asp Ser
        675                 680                 685

Pro Arg Asp Leu Met Val Thr Ala Ser Ser Glu Thr Ser Ile Ser Leu
    690                 695                 700

Ile Trp Thr Lys Ala Ser Gly Pro Ile Asp His Tyr Arg Ile Thr Phe
705                 710                 715                 720

Thr Pro Ser Ser Gly Ile Ala Ser Glu Val Thr Val Pro Lys Asp Arg
                725                 730                 735

Thr Ser Tyr Thr Leu Thr Asp Leu Glu Pro Gly Ala Glu Tyr Ile Ile
            740                 745                 750

Ser Val Thr Ala Glu Arg Gly Arg Gln Gln Ser Leu Glu Ser Thr Val
        755                 760                 765

Asp Ala Phe Thr Gly Phe Arg Pro Ile Ser His Leu His Phe Ser His
    770                 775                 780

Val Thr Ser Ser Ser Val Asn Ile Thr Trp Ser Asp Pro Ser Pro Pro
785                 790                 795                 800

Ala Asp Arg Leu Ile Leu Asn Tyr Ser Pro Arg Asp Glu Glu Glu Glu
                805                 810                 815

Met Met Glu Val Ser Leu Asp Ala Thr Lys Arg His Ala Val Leu Met
            820                 825                 830

Gly Leu Gln Pro Ala Thr Glu Tyr Ile Val Asn Leu Val Ala Val His
        835                 840                 845

Gly Thr Val Thr Ser Glu Pro Ile Val Gly Ser Ile Thr Thr Gly Ile
    850                 855                 860

Asp Pro Pro Lys Asp Ile Thr Ile Ser Asn Val Thr Lys Asp Ser Val
865                 870                 875                 880

Met Val Ser Trp Ser Pro Pro Val Ala Ser Phe Asp Tyr Tyr Arg Val
                885                 890                 895

Ser Tyr Arg Pro Thr Gln Val Gly Arg Leu Asp Ser Ser Val Val Pro
            900                 905                 910

Asn Thr Val Thr Glu Phe Thr Ile Thr Arg Leu Asn Pro Ala Thr Glu
        915                 920                 925

Tyr Glu Ile Ser Leu Asn Ser Val Arg Gly Arg Glu Glu Ser Glu Arg
    930                 935                 940

Ile Cys Thr Leu Val His Thr Ala Met Asp Asn Pro Val Asp Leu Ile
945                 950                 955                 960

Ala Thr Asn Ile Thr Pro Thr Glu Ala Leu Leu Gln Trp Lys Ala Pro
                965                 970                 975

Val Gly Glu Val Glu Asn Tyr Val Ile Val Leu Thr His Phe Ala Val
            980                 985                 990

Ala Gly Glu Thr Ile Leu Val Asp  Gly Val Ser Glu Glu  Phe Arg Leu
        995                 1000                1005

Val Asp  Leu Leu Pro Ser Thr  His Tyr Thr Ala Thr  Met Tyr Ala
```

-continued

```
                 1010                1015                1020
    Thr  Asn  Gly  Pro  Leu  Thr  Ser  Gly  Thr  Ile  Ser  Thr  Asn  Phe  Ser
                 1025                1030                1035

Thr  Leu  Leu  Asp  Pro  Pro  Ala  Asn  Leu  Thr  Ala  Ser  Glu  Val  Thr
                 1040                1045                1050

Arg  Gln  Ser  Ala  Leu  Ile  Ser  Trp  Gln  Pro  Pro  Arg  Ala  Glu  Ile
                 1055                1060                1065

Glu  Asn  Tyr  Val  Leu  Thr  Tyr  Lys  Ser  Thr  Asp  Gly  Ser  Arg  Lys
                 1070                1075                1080

Glu  Leu  Ile  Val  Asp  Ala  Glu  Asp  Thr  Trp  Ile  Arg  Leu  Glu  Gly
                 1085                1090                1095

Leu  Leu  Glu  Asn  Thr  Asp  Tyr  Thr  Val  Leu  Leu  Gln  Ala  Ala  Gln
                 1100                1105                1110

Asp  Thr  Thr  Trp  Ser  Ser  Ile  Thr  Ser  Thr  Ala  Phe  Thr  Thr  Gly
                 1115                1120                1125

Gly  Arg  Val  Phe  Pro  His  Pro  Gln  Asp  Cys  Ala  Gln  His  Leu  Met
                 1130                1135                1140

Asn  Gly  Asp  Thr  Leu  Ser  Gly  Val  Tyr  Pro  Ile  Phe  Leu  Asn  Gly
                 1145                1150                1155

Glu  Leu  Ser  Gln  Lys  Leu  Gln  Val  Tyr  Cys  Asp  Met  Thr  Thr  Asp
                 1160                1165                1170

Gly  Gly  Gly  Trp  Ile  Val  Phe  Gln  Arg  Arg  Gln  Asn  Gly  Gln  Thr
                 1175                1180                1185

Asp  Phe  Phe  Arg  Lys  Trp  Ala  Asp  Tyr  Arg  Val  Gly  Phe  Gly  Asn
                 1190                1195                1200

Val  Glu  Asp  Glu  Phe  Trp  Leu  Gly  Leu  Asp  Asn  Ile  His  Arg  Ile
                 1205                1210                1215

Thr  Ser  Gln  Gly  Arg  Tyr  Glu  Leu  Arg  Val  Asp  Met  Arg  Asp  Gly
                 1220                1225                1230

Gln  Glu  Ala  Ala  Phe  Ala  Ser  Tyr  Asp  Arg  Phe  Ser  Val  Glu  Asp
                 1235                1240                1245

Ser  Arg  Asn  Leu  Tyr  Lys  Leu  Arg  Ile  Gly  Ser  Tyr  Asn  Gly  Thr
                 1250                1255                1260

Ala  Gly  Asp  Ser  Leu  Ser  Tyr  His  Gln  Gly  Arg  Pro  Phe  Ser  Thr
                 1265                1270                1275

Glu  Asp  Arg  Asp  Asn  Asp  Val  Ala  Val  Thr  Asn  Cys  Ala  Met  Ser
                 1280                1285                1290

Tyr  Lys  Gly  Ala  Trp  Trp  Tyr  Lys  Asn  Cys  His  Arg  Thr  Asn  Leu
                 1295                1300                1305

Asn  Gly  Lys  Tyr  Gly  Glu  Ser  Arg  His  Ser  Gln  Gly  Ile  Asn  Trp
                 1310                1315                1320

Tyr  His  Trp  Lys  Gly  His  Glu  Phe  Ser  Ile  Pro  Phe  Val  Glu  Met
                 1325                1330                1335

Lys  Met  Arg  Pro  Tyr  Asn  His  Arg  Leu  Met  Ala  Gly  Arg  Lys  Arg
                 1340                1345                1350

Gln  Ser  Leu  Gln  Phe
                 1355
```